(12) United States Patent
Drew et al.

(10) Patent No.: US 10,092,591 B2
(45) Date of Patent: Oct. 9, 2018

(54) METHODS AND COMPOSITIONS FOR THE TREATMENT OF ISCHEMIC INJURY TO TISSUE USING THERAPEUTIC HYPOTHERMIA

(71) Applicant: University of Alaska Fairbanks, Fairbanks, AK (US)

(72) Inventors: Kelly Drew, Fairbanks, AK (US); Tulasi Jinka, Ann Arbor, MI (US); Lori Bogren, North Pole, AK (US); Isaac Bailey, Fairbanks, AK (US); Zachary Carlson, Fairbanks, AK (US); Jasmine Olson, Shoreline, WA (US)

(73) Assignee: University of Alaska Fairbanks, Fairbanks, AK (US)

( * ) Notice: Subject to any disclaimer, the term of this patent is extended or adjusted under 35 U.S.C. 154(b) by 647 days.

(21) Appl. No.: 14/191,515

(22) Filed: Feb. 27, 2014

(65) Prior Publication Data
US 2015/0238513 A1 Aug. 27, 2015

(51) Int. Cl.
| | | |
|---|---|---|
| A61K 31/7076 | (2006.01) | |
| A61K 31/00 | (2006.01) | |
| A61K 45/06 | (2006.01) | |
| A61K 31/52 | (2006.01) | |
| A61K 31/44 | (2006.01) | |
| A61K 38/57 | (2006.01) | |
| A61K 31/661 | (2006.01) | |
| A61K 31/155 | (2006.01) | |
| A61K 31/166 | (2006.01) | |
| A61K 31/366 | (2006.01) | |
| C07D 473/06 | (2006.01) | |
| A61K 31/4439 | (2006.01) | |
| A61K 31/522 | (2006.01) | |

(52) U.S. Cl.
CPC .......... *A61K 31/7076* (2013.01); *A61K 31/00* (2013.01); *A61K 31/4439* (2013.01); *A61K 31/522* (2013.01); *A61K 31/166* (2013.01); *A61K 31/366* (2013.01); *A61K 31/661* (2013.01); *A61K 38/57* (2013.01); *A61K 45/06* (2013.01); *C07D 473/06* (2013.01)

(58) Field of Classification Search
CPC .... A61K 31/7076; A61K 31/00; A61K 45/06; A61K 47/481; A61K 31/675; A61K 31/52; A61K 2300/00; A61K 31/44; A61K 38/57; A61K 31/4439; A61K 31/661; A61K 31/155; A61K 31/166; A61K 31/185; A61K 31/366; C07D 473/06
See application file for complete search history.

(56) References Cited

U.S. PATENT DOCUMENTS

| | | | | |
|---|---|---|---|---|
| 4,904,472 A | | 2/1990 | Belardinelli | 514/263 |
| 5,069,985 A | | 12/1991 | Cohen | 429/26 |
| 5,504,090 A | * | 4/1996 | Neely | A61K 31/00 435/1.2 |
| 5,573,772 A | * | 11/1996 | Downey | A61K 31/70 424/423 |
| 5,733,916 A | * | 3/1998 | Neely | A61K 31/00 514/263.3 |
| 6,001,842 A | * | 12/1999 | Neely | A61K 31/00 514/171 |
| 6,211,165 B1 | * | 4/2001 | Liang | A61K 31/00 514/46 |
| 6,316,423 B1 | | 11/2001 | Von Lubitz | 514/46 |
| 6,545,002 B1 | * | 4/2003 | Linden | C07D 473/06 514/263.2 |
| 6,586,413 B2 | * | 7/2003 | Liang | A61K 31/00 514/46 |
| 8,188,063 B2 | * | 5/2012 | Li | A61K 31/519 514/42 |
| 2003/0092668 A1 | * | 5/2003 | Liang | A61K 31/00 514/46 |
| 2004/0121406 A1 | * | 6/2004 | Wilson | A61K 31/739 435/7.1 |
| 2006/0205671 A1 | * | 9/2006 | Vinten-Johansen | A61K 31/185 514/1.3 |
| 2007/0213295 A1 | | 9/2007 | Lee | 514/47 |
| 2008/0097385 A1 | * | 4/2008 | Vinten-Johansen | A61K 31/155 604/509 |
| 2009/0048199 A1 | | 2/2009 | Marr | 514/44 |
| 2009/0325878 A1 | | 12/2009 | Dobson | 514/12 |
| 2011/0262442 A1 | * | 10/2011 | Hamilton | A61K 31/7076 424/139.1 |
| 2013/0224110 A1 | * | 8/2013 | Bynoe | A61K 31/706 424/1.49 |

FOREIGN PATENT DOCUMENTS

| | | |
|---|---|---|
| EP | 1 385 523 | 2/2004 |
| WO | WO 2000/056145 | 9/2000 |
| WO | WO 2002/089736 | 11/2002 |
| WO | WO 2004/056180 | 7/2004 |
| WO | WO 2008/116308 | 10/2008 |
| WO | WO 2009/071094 | 6/2009 |
| WO | WO 2009/071095 | 6/2009 |

(Continued)

OTHER PUBLICATIONS

Blight Nat. Neurosci. 2002. 5: 1051-4.*
Schmidt et al. Annu. Rev. Biomed. Eng. 2003. 5: 293-347.*
Hoke et al. Nat. Clin. Pract. Neurol. 2006: 448-454.*
Burgess et al. J of Cell Bio. 1990, 111:2129-2138.*
Bowie et al. Science, 1990, 247:1306-1310.*
Pawson et al. 2003, Science 300:445-452.*
Bauer et al., J. Nucl. Med., 2003; 44:1682-1689.*
Reichelt et al. Exp. Physiol. 2007; 92:175-185.*
von Lubitz et al. J. Mol. Neurosci. 1990; 2:53-59.*
Maczewski et al. J. Mol. Cell Cardiol. 1998; 30:1735-1747.*

(Continued)

*Primary Examiner* — Chang-Yu Wang
(74) *Attorney, Agent, or Firm* — Ballard Spahr LLP

(57) ABSTRACT

Disclosed are compositions and methods for inducing therapeutic hypothermia in a subject.

8 Claims, 13 Drawing Sheets

(56) References Cited

FOREIGN PATENT DOCUMENTS

| WO | WO 2009/071096 | 6/2009 |
| WO | WO 2010/015260 | 2/2010 |

OTHER PUBLICATIONS

Alam MN, et al. (2009) Role of adenosine A(1) receptor in the perifornical-lateral hypothalamic area in sleep-wake regulation in rats. Brain Res. 1304:96-104.
Anderson R, et al. (1994) Characterization of the adenosine receptors mediating hypothermia in the conscious mouse. Br J Pharmacol. 113:1386-1390.
Arrich J, et al. (2009) Hypothermia for neuroprotection in adults after cardiopulmonary resuscitation. Cochrane Database Syst Rev. CD004128.
Barnes BM, (1989) Freeze avoidance in a mammal: Body temperatures below 0 degree c in an arctic hibernator. Science. 244:1593-1595.
Barros RC, et al. (2006) Respiratory and body temperature modulation by adenosine A1 receptors in the anteroventral preoptic region during normoxia and hypoxia. Respir Physiol Neurobiol. 153:115-125.
Benington JH, et al. (1995) Stimulation of A1 adenosine receptors mimics the electroencephalographic effects of sleep deprivation. Brain Res. 692:79-85.
Bernard SA, et al. (2002) Treatment of comatose survivors of out-of-hospital cardiac arrest with induced hypothermia. N Engl J Med. 346(8):557-563.
Bischofberger N, et al. (1997) Adenosine a1 receptor agonists as clinically viable agents for treatment of ischemic brain disorders. Ann N Y Acad Sci. 825:23-29.
Blackstone E, et al. (2005) H2S induces a suspended animation-like state in mice. Science. 308, 518.
Boison D, et al. (2011) Homeostatic bioenergetic network regulation: a novel concept to avoid pharmacoresistance in epilepsy. Expert Opin Drug Discov. 6(7):713-724.
Bott-Flugel L, et al. (2011) Selective attenuation of norepinephrine release and stress-induced heart rate increase by partial adenosine a1 agonism. PLoS One. 6(3):e18048.
Bratincsak A, et al. (2007) Spatial and temporal activation of brain regions in hibernation: c-fos expression during the hibernation bout in thirteen lined ground squirrel. J Comp Neurol. 505(4):443-458.
Buck CL, et al. (2000) Effects of ambient temperature on metabolic rate, respiratory quotient, and torpor in an arctic hibernator. Am J Physiol Regul Integr Comp Physiol. 279:R255-262.
Busto R, et al. (1987) Small differences in intraischemic brain temperature critically determine the extent of ischemic neuronal injury. J Cereb Blood Flow Metab. 7:729-738.
Cheung JW, et al. (2003) Cvt-510: A selective a1 adenosine receptor agonist. Cardiovasc Drug Rev. 21(4):277-292.
Constantinescu AO, et al. (2011) Endogenous adenosine A1 receptor activation underlies the transient post-ischemic rhythmic delta EEG activity. Clin Neurophysiol. 122(6):1117-1126.
Dag KJE von Lubitz DK. (2001) Adenosine in the treatment of stroke: yes, maybe, or absolutely not? Expert Opin Investig Drugs. 10(4):619-632.
Daniels IS, et al. (2010) A role of erythrocytes in adenosine monophosphate initiation of hypometabolism in mammals. J Biol Chem. 285:20716-20723.
Dave KR, et al. (2006) The arctic ground squirrel brain is resistant to injury from cardiac arrest during euthermia Stroke. 37(5):261-1265.
Dias da Silva VJ. et al. (2012) Acute adenosine increases cardiac vagal and reduces sympathetic efferent nerve activities in rats. Exp Physiol. 97:719-729.
Drew KL, et al. (2012) Chapter 13. The bioenergetic network of adenosine in hibernation, sleep and thermoregulation. In Adenosine: a Key Link between Metabolism and CNS Activity, S.A. Masino, and D. Boison, eds. (New York, Springer), pp. 252-372.
Dunwiddie TV, et al. (2001) The role and regulation of adenosine in the central nervous system. Annu Rev Neurosci. 24:31-55.
Dworak M, et al. (2010) Sleep and brain energy levels: ATP changes during sleep. J Neurosci. 30:9007-9016.
Evoniuk G, et al. (1987) Antagonism of the cardiovascular effects of adenosine by caffeine or 8-(p-sulfophenyl)theophylline. J Pharmacol Exp Ther. Feb;240(2):428-32.
Faridar A, et al. (2011) Therapeutic hypothermia in stroke and traumatic brain injury. Front Neurol. 2:80.
Featherstone RL, et al. (2004) Long-term hypothermic lung preservation: does adenosine A1 receptor antagonism have a role in ischemic preconditioning protection? Interact Cardiovasc Thorac Surg. 3(1):182-187.
Geiser F. (1988) Reduction of metabolism during hibernation and daily torpor in mammals and birds: Temperature effect or physiological inhibition? J Comp Physiol B. 158:25-37.
Gerashchenko D, et al. (2011) Sleep-active cells in the cerebral cortex and their role in slow-wave activity. Sleep Biol Rhythms. 9:71-77.
Halle JN, et al. (1997) Enhancing adenosine A1 receptor binding reduces hypoxic-ischemic brain injury in newborn rats. Brain Res. 759(2):309-312.
Harris MB, et al. (1995) Parasympathetic influence on heart rate in euthermic and hibernating ground squirrels. J Exp Biol. 198:931-937.
Haugk M, et al. (2011) Relationship between time to target temperature and outcome in patients treated with therapeutic hypothermia after cardiac arrest. Crit Care. 15(2):R101.
Heller HC, et al. (1977) Thermoregulation during entrance into hibernation. Pflügers Arch. 369:55-59.
Hypothermia-after-Cardiac-Arrest-Study-Group (2002) Mild therapeutic hypothermia to improve the neurologic outcome after cardiac arrest. N Engl J Med. 346:549-556.
Iliff BW, et al. (2012) Central adenosine receptor signaling is necessary for daily torpor in mice. Am J Physiol Regul Integr Comp Physiol. 303:R477-484.
Januszewicz von Lubitz DK, et al. (1989) Protective effect of cyclohexyl adenosine in treatment of cerebral ischemia in gerbils. Neuroscience. 30(2):451-462.
Jinka TR, et al. (2010) Altered thermoregulation via sensitization of A1 adenosine receptors in dietary-restricted rats. Psychopharmacology (Berl). 209:217-224.
Jinka TR, et al. (2011) Season primes the brain in an arctic hibernator to facilitate entrance into torpor mediated by adenosine a(1) receptors. J Neurosci. 31:10752-10758.
Jordan JD, et al. (2007) Hypothermia: comparing technology. J Neurol Sci. 261:35-38.
Katz L, et al. (1995) Outcome model of asphyxial cardiac arrest in rats. J Cereb Blood Flow Metab. 15:1032-1039.
Kirschner DL, et al. (2009) Simultaneous efflux of endogenous D-ser and L-glu from single acute hippocampus slices during oxygen glucose deprivation. J Neurosci Res. 87(12):2812-2820.
Kliegel A, et al. (2007) Cold infusions alone are effective for induction of therapeutic hypothermia but do not keep patients cool after cardiac arrest. Resuscitation. 73:46-53.
Korboukh I, et al. (2012) Orally active adenosine a(1) receptor agonists with antinociceptive effects in mice. J Med Chem. 55(14):6467-6477.
Kumar S, et al. (2011) Central nervous system sites of the sleep promoting effects of eszopiclone in rats. Neuroscience. 181:67-78.
Liu GS, et al. (1991) Protection against infarction afforded by preconditioning is mediated by a1 adenosine receptors in rabbit heart. Circulation. 84:350-356.
Logan A, et al. (2011) Optimal management of shivering during therapeutic hypothermia after cardiac arrest. Crit Care Nurse. 31:e18-30.
Lusardi TA, et al. (2012) Caffeine prevents acute mortality after TBI in rats without increased morbidity. Exp Neurol. 234(1):161-168.
Lyman CP, et al. (1963) Autonomic control of circulation during the hibernating cycle in ground squirrels. J Physiol. 168:477-499.
Malhotra J, et al. (1997) Effect of adenosine receptor modulation on pentylenetetrazole-induced seizures in rats. Br J Pharmacol. 120(2):282-288.

(56) References Cited

OTHER PUBLICATIONS

Matuszek M, et al. (1986) The effect of N6-cyclohexyladenosine and 5'-N-ethylcarboxamidoadenosine on body temperature in normothermic rabbits. Gen Pharmacol. 27(3):467-469.
Miller LP, et al. (1992) Therapeutic potential for adenosine receptor activation in ischemic brain injury. J Neurotrauma. 9 Suppl 2:S563-S577.
Miyazawa S, et al. (2008) Central A1-receptor activation associated with onset of torpor protects the heart against low temperature in the Syrian hamster. Am J Physiol Regul Integr Comp Physiol. 295(3):R991-R996.
Olson JM, et al. (2013) Circannual rhythm in body temperature, torpor, and sensitivity to a(1) adenosine receptor agonist in arctic ground squirrels. J Biol Rhythms. 28:201-207.
Popov V, et al. (2011) Suspension of mitotic activity in dentate gyrus of the hibernating ground squirrel. Neural Plast. 2011:867525.
Porkka-Heiskanen T, et al. (2011) Adenosine, energy metabolism and sleep homeostasis. Sleep Med Rev. 15:123-135.
Rai S, et al. (2010) A1 receptor mediated adenosinergic regulation of perifornical-lateral hypothalamic area neurons in freely behaving rats. Neuroscience. 167:40-48.
Rittiner JE, et al. (2012) Amp is an adenosine a1 receptor agonist. J Biol Chem. 287:5301-5309.
Roman V, et al. (2008) Repetitive stimulation of adenosine A1 receptors in vivo: changes in receptor numbers, G-proteins and A1 receptor agonist-induced hypothermia. Brain Res. 1191:69-74.
Rudolphi KA, et al. (1992) Adenosine and brain ischemia. Cerebrovasc Brain Metab Rev. 4(4):346-369.
Sessler DI, et al. (2009) Defeating normal thermoregulatory defenses: induction of therapeutic hypothermia. Stroke. 40:e614-621.
Seupaul RA, et al. (2011) Evidence-based emergency medicine. Does therapeutic hypothermia benefit survivors of cardiac arrest? Ann Emerg Med. 58:282-283.
Shao C, et al. (2010) Shotgun proteomics analysis of hibernating arctic ground squirrels. Mol Cell Proteomics. 9(2):313-326.
Shin R, et al. (2010) Administration of the GABAA receptor antagonist picrotoxin into rat supramammillary nucleus induces c-Fos in reward-related brain structures. Supramammillary picrotoxin and c-Fos expression. BMC Neurosci. 11:101.
Shintani M, et al. (2005) Characterization of N(6)-cyclohexyladenosine-induced hypothermia in Syrian hamsters. J Pharmacol Sci. 97:451-454.
Sorimachi T, et al. (2004) Pharmacological manipulations of ATP-dependent potassium channels and adenosine A1 receptors do not impact hippocampal ischemic preconditioning in vivo: evidence in a highly quantitative gerbil model. J Cereb Blood Flow Metab. 24(5):556-563.
Swoap SJ, et al. (2007) AMP does not induce torpor. Am J Physiol Regul Integr Comp Physiol. 293:R468-473.
Szymusiak R, et al. (2008) Hypothalamic regulation of sleep and arousal. Ann N Y Acad Sci. 1129:275-286.
Tamura Y, et al. (2005) Phase-specific central regulatory systems of hibernation in syrian hamsters. Brain Res. 1045:88-96.
Tao Z, et al. (2011) 5'-Adenosine monophosphate induced hypothermia reduces early stage myocardial ischemia/reperfusion injury in a mouse model. Am J Transl Res. 3(4):351-361.
Tendera M, et al. (2012) The new oral adenosine A1 receptor agonist capadenoson in male patients with stable angina. Clin Res Cardio. 101:585-591.
Testori C, et al. (2011) Surface cooling for induction of mild hypothermia in conscious healthy volunteers—a feasibility trial. Crit Care. 15:R248.
Ticho SR, et al. (1991) Role of adenosine in sleep and temperature regulation in the preoptic area of rats. Pharmacol Biochem Behav. 40(1):33-40.
Toien O, et al. (2011) Hibernation in black bears: independence of metabolic suppression from body temperature. Science. 331:906-909.
Tupone D, et al. (2013) Central activation of the a1 adenosine receptor (a1ar) induces a hypothermic, torpor-like state in the rat. J Neurosci. 33(36):14512-14525.
Ukena D, et al. (1986) Species differences in structure-activity relationships of adenosine agonists and xanthine antagonists at brain A1 adenosine receptors. FEBS Lett. 209(1):122-128.
Uray T, et al. (2008) Out-of-hospital surface cooling to induce mild hypothermia in human cardiac arrest: A feasibility trial. Resuscitation. 77:331-338.
von Lubitz DK, et al. (1990) Cerebral ischemia in gerbils: postischemic administration of cyclohexyl adenosine and 8-sulfophenyl-theophylline. J Mol Neurosci. 2(1):53-59.
Von Lubitz DK, et al. (1996) Postischemic administration of adenosine amine congener (ADAC): analysis of recovery in gerbils. Eur J Pharmacol. 316(2-3):171-179.
Walker JM, et al. (1977) Sleep and hibernation in ground squirrels (*Citellus* spp): electrophysiological observations. Am J Physiol. 233:R213-221.
Walker JM, et al. (1980) Hibernation and circannual rhythms of sleep. Physiological Zoology. 53:8-11.
Xu K, et al. (2006) Adenosine treatment delays postischemic hippocampal CA1 loss after cardiac arrest and resuscitation in rats. Brain Res. 1071(1):208-217.
Yuan HB, et al. (2004) Hypothermic preconditioning increases survival of purkinje neurons in rat cerebellar slices after an in vitro simulated ischemia. Anesthesiology. 100(2):331-337.
Yunoki M, et al. (2003) Hypothermic preconditioning induces rapid tolerance to focal ischemic injury in the rat. Exp Neurol. 181(2):291-300.
Zgavc T, et al. (2011) Experimental and clinical use of therapeutic hypothermia for ischemic stroke: Opportunities and limitations. Stroke Res Treat. 2011:689290 (9 pages).
Zhang J, et al. (2006) Constant darkness is a circadian metabolic signal in mammals. Nature. 439:340-343.
Zhao HW, et al. (2006) Distribution of NMDA receptor subunit NR1 in arctic ground squirrel central nervous system. J Chem Neuroanat. 32:196-207.

\* cited by examiner

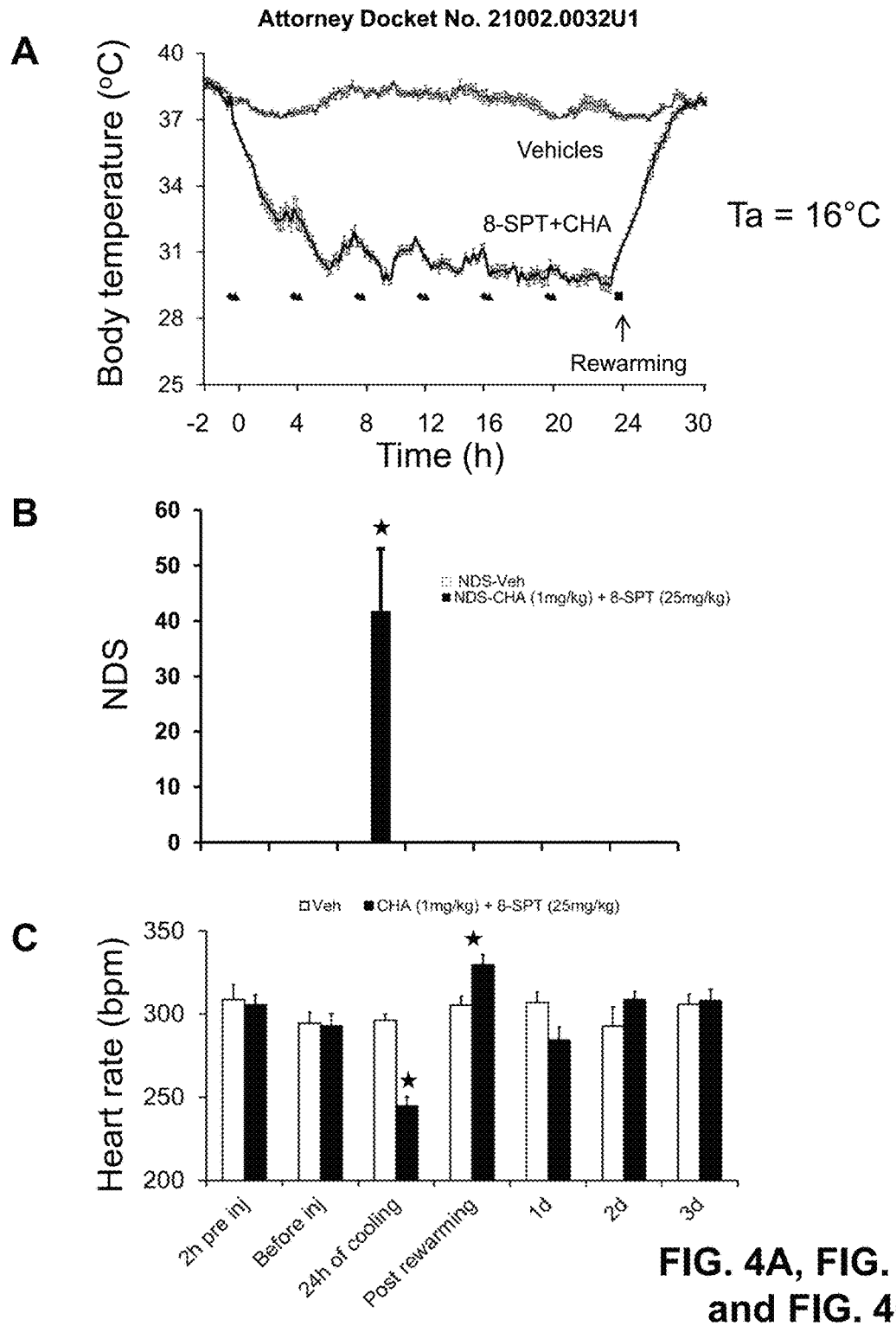
FIG. 4A, FIG. 4B, and FIG. 4C

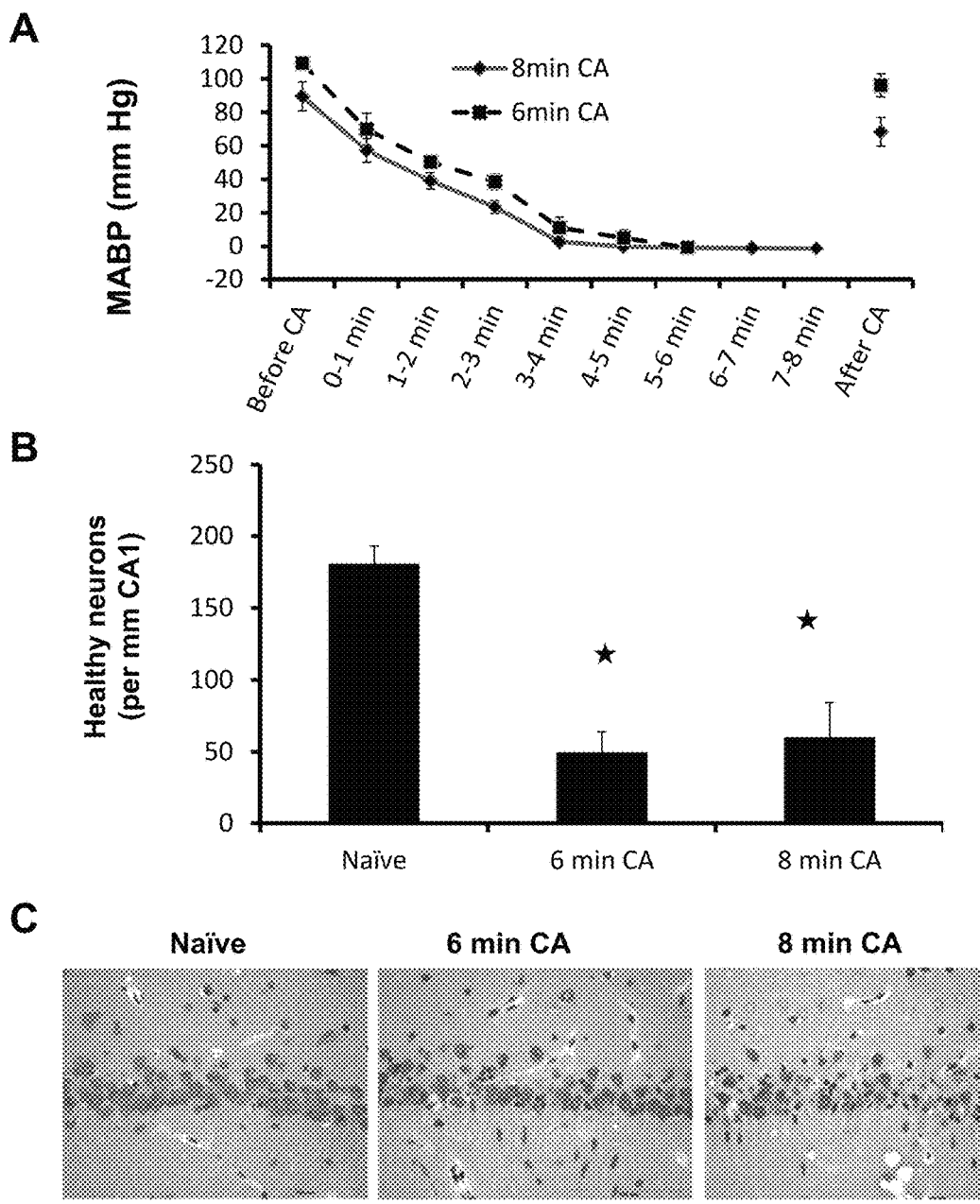
FIG. 7A, FIG. 7B, and FIG. 7C

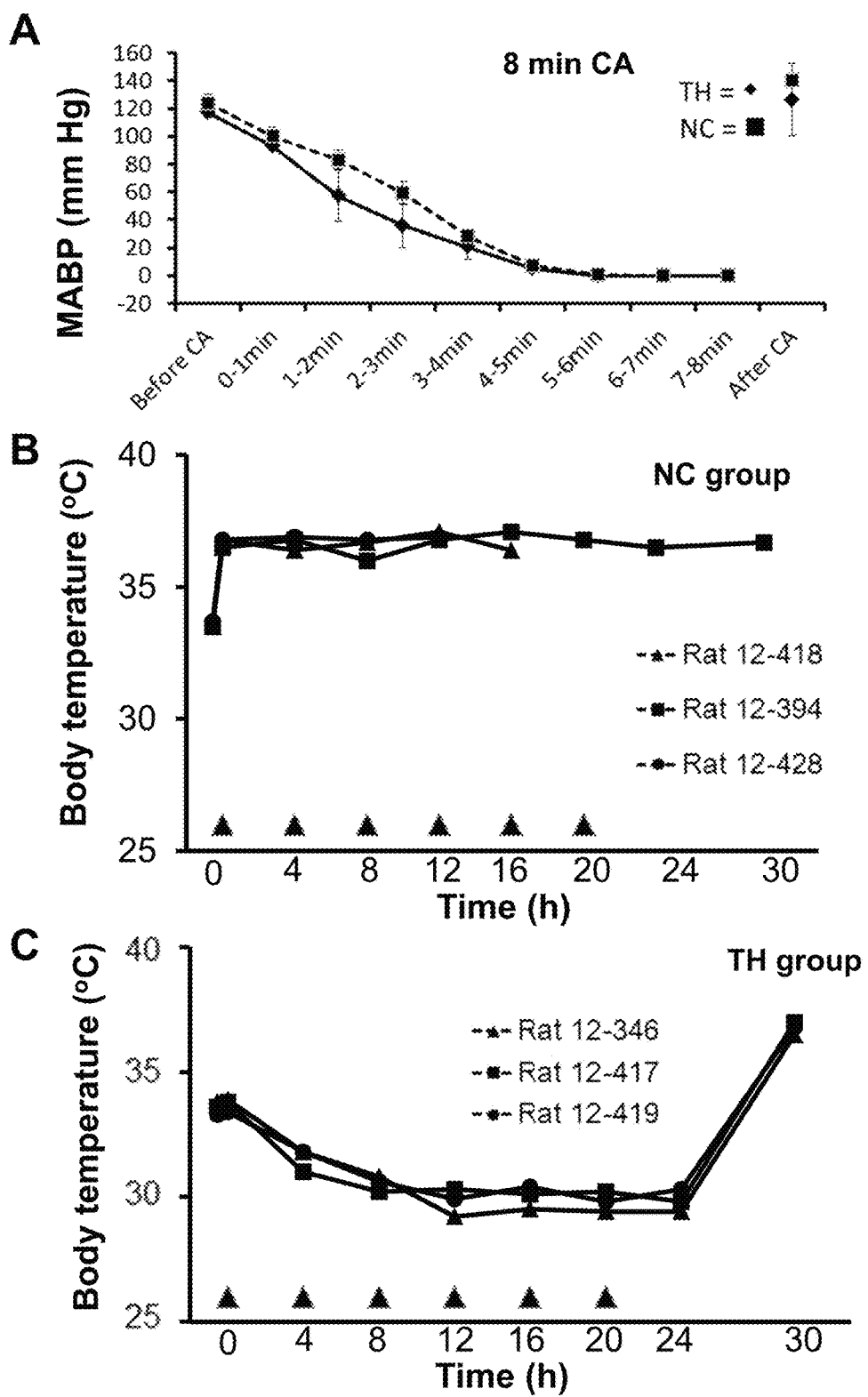
FIG. 8A, FIG. 8B, and FIG. 8C

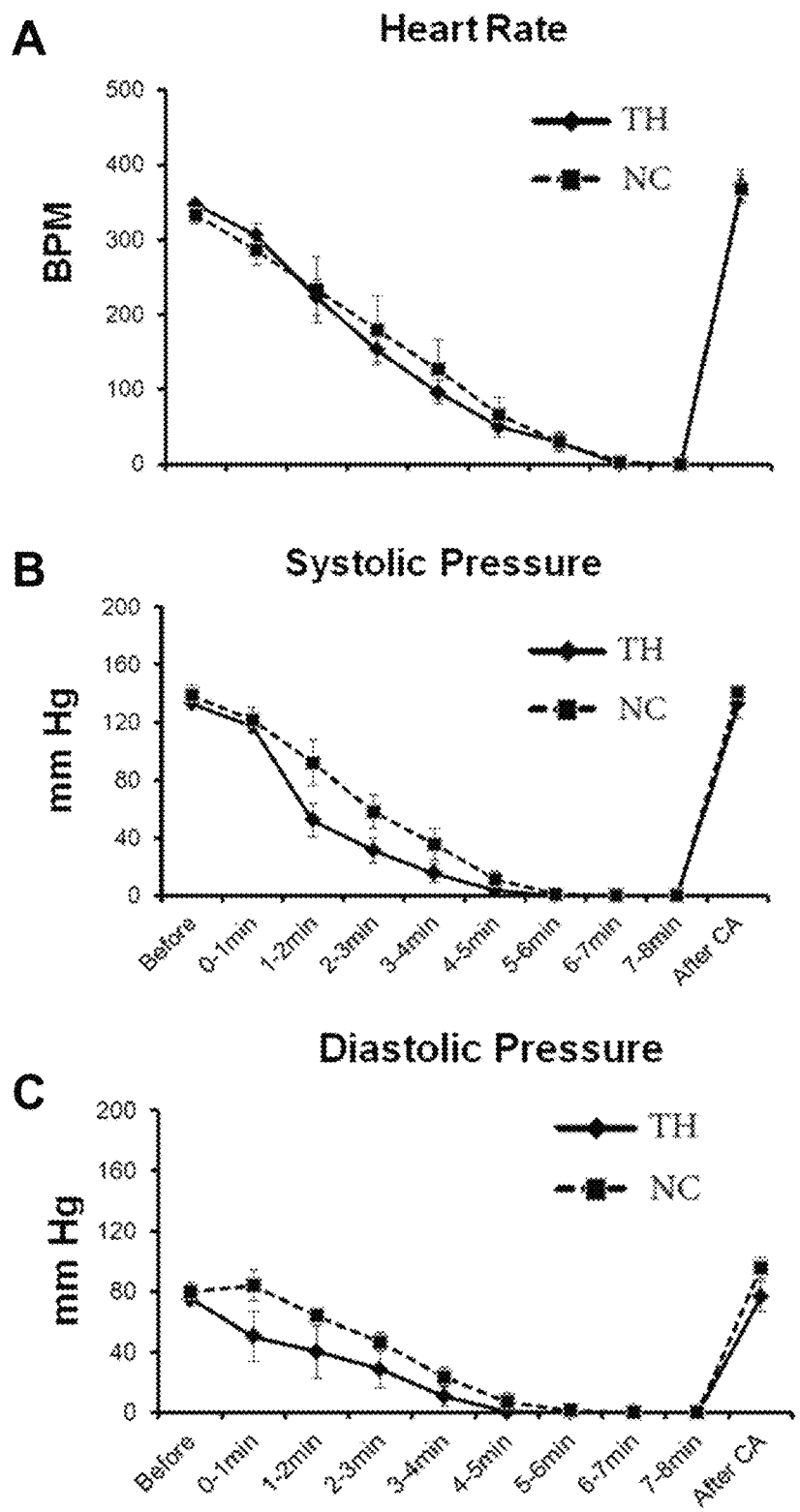
FIG. 10A, FIG. 10B, and FIG. 10C

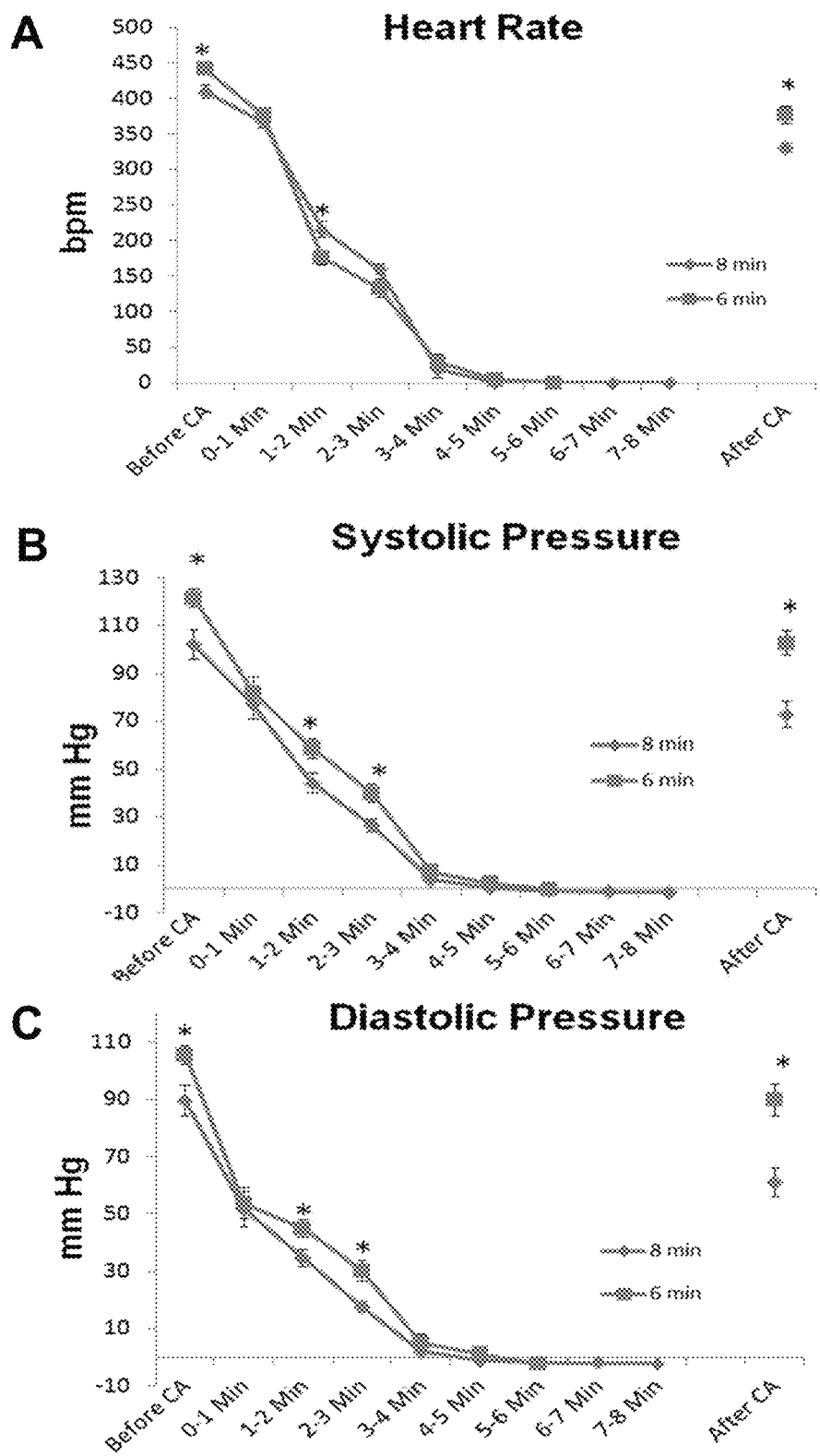
FIG. 11A, FIG. 11B, and FIG. 11C

METHODS AND COMPOSITIONS FOR THE TREATMENT OF ISCHEMIC INJURY TO TISSUE USING THERAPEUTIC HYPOTHERMIA

STATEMENT REGARDING FEDERALLY SPONSORED RESEARCH OR DEVELOPMENT

This invention was made with government support under Grant No. R15NS070779 awarded by National Institute of Neurological Disorders and Stroke. The government has certain rights in the invention.

BACKGROUND OF THE INVENTION

Ischemia is the lack of oxygenated blood flow to various body parts and organs. Cerebral ischemia is an ischemic condition where the brain or parts of the brain do not receive enough blood flow to maintain normal neurological function. Cerebral ischemia can be the result of various serious diseases such as stroke and cardiac arrest or the result of arterial obstruction such as strangulation. Severe or prolonged cerebral ischemia results in unconsciousness, brain damage, or death.

Therapeutic hypothermia has been shown to minimize brain injury and improve prognosis after cardiac arrest (CA). Mild therapeutic hypothermia, which involves decreasing core body temperature (Tb) to between 32-34° C. within 2 hr of restoration of spontaneous circulation (ROSC) and maintaining reduced Tb for 12-24 hr, is currently the only clinical intervention available for global cerebral ischemia (Hypothermia-after-Cardiac-Arrest-Study-Group, 2002; Seupaul and Wilbur, 2011). The clinical benefit of mild therapeutic hypothermia following focal cerebral ischemia is less clear (Bi et al., 2011; Faridar et al., 2011), but cooling shows obvious benefits in animal models of ischemic stroke (Busto et al., 1987). The fact that therapeutic hypothermia has not so far shown benefits in stroke trials may stem from failure to achieve Tb's between 32-34° C. (Faridar et al., 2011; Jordan and Carhuapoma, 2007). Shivering is the most problematic issue in achieving and maintaining hypothermia using conventional technology that relies on external or internal cooling mechanisms such as ice packs or i.v. infusion of cold saline. Shivering counteracts efforts to lower Tb and can be exceedingly uncomfortable for awake patients, such as those with a typical ischemic stroke (Sessler, 2009). Using standard pharmacotherapies to suppress shivering, current cooling techniques achieve core body temperature of only 35° C. in patients with acute ischemic stroke (Kollmar et al., 2009) or conscious healthy volunteers (Testori et al., 2011). What is needed are methods and compositions for inducing therapeutic hypothermia to facilitate treating or preventing ischemic brain damage.

BRIEF SUMMARY OF THE INVENTION

Disclosed herein are methods and compositions related to the induction of hypothermia in a predictable and dose responsive fashion by use of a pharmaceutical composition comprising at least one compound capable of inducing hypothermia, thereby benefiting patients suffering from illnesses characterized by ischemic tissue damage.

Disclosed herein are methods of inducing therapeutic hypothermia in a subject comprising administering to the subject a therapeutically effective amount of one or more $A_1$ adenosine receptor ($A_1AR$) agonists and one or more $A_1AR$ antagonists.

Disclosed herein are methods of inducing therapeutic hypothermia of any preceding embodiment, wherein the subject has an ischemic brain injury or has suffered an ischemic stroke, cardiac arrest, hemorrhagic shock, traumatic injury including brain injury, seizure activity, and/or epilepsy; or wherein the subject requires treatment for drug addiction, post-traumatic stress disorder, depression or other mental health conditions involving impaired or altered neural plasticity; or wherein sleep, sedative or anxiolytic effects are needed.

Disclosed herein are methods of inducing therapeutic hypothermia of any preceding embodiment, wherein the subject is conscious or not comatose.

Disclosed herein are methods of inducing therapeutic hypothermia of any preceding embodiment, wherein the $A_1AR$ agonist crosses the blood brain barrier.

Disclosed herein are methods of inducing therapeutic hypothermia of any preceding embodiment, wherein the $A_1AR$ agonist is $N^6$-cyclohexyladenosine (CHA) or capadenoson.

Disclosed herein are methods of inducing therapeutic hypothermia of any preceding embodiment, wherein the $A_1AR$ antagonist does not cross the blood-brain barrier.

Disclosed herein are methods of inducing therapeutic hypothermia of any preceding embodiment, wherein the $A_1AR$ antagonist is 8-p-sulfophenyltheophylline (8-SPT).

Disclosed herein are methods of inducing therapeutic hypothermia of any preceding embodiment, wherein the one or more $A_1AR$ agonists and the one or more $A_1AR$ antagonists are co-administered or the antagonist is titrated to minimize side effects of the agonist.

Disclosed herein are methods of inducing therapeutic hypothermia of any preceding embodiment, wherein the $A_1AR$ agonist is $N^6$-cyclohexyladenosine (CHA) or capadenoson and the $A_1AR$ antagonist is 8-p-sulfophenyltheophylline (8-SPT).

Disclosed herein are methods of inducing therapeutic hypothermia of any preceding embodiment, wherein the one or more $A_1AR$ agonists or $A_1AR$ antagonists are administered to the subject intraperitoneally.

Disclosed herein are methods of inducing therapeutic hypothermia of any preceding embodiment, wherein the one or more $A_1AR$ agonists or $A_1AR$ antagonists are administered to the subject intravenously, subcutaneously, intramuscularly, by cutaneous patch or orally.

Disclosed herein are methods of inducing therapeutic hypothermia of any preceding embodiment, further comprising maintaining hypothermia in the subject.

Disclosed herein are methods of inducing therapeutic hypothermia of any preceding embodiment, wherein maintaining hypothermia in the subject comprises repeating the administration of the one or more $A_1AR$ agonists or $A_1AR$ antagonists.

Disclosed herein are methods of enhancing the induction of therapeutic hypothermia in a subject comprising administering to the subject a therapeutically effective amount of one or more $A_1AR$ agonists and one or more $A_1AR$ antagonists, wherein the subject is fed a restrictive diet for a predetermined time period prior to the administration of the one or more $A_1AR$ agonists and the one or more $A_1AR$ antagonists.

Disclosed herein are methods of enhancing the induction of therapeutic hypothermia of enhancing the induction of any preceding embodiment, wherein the subject is fed every other day.

Disclosed herein are methods of enhancing the induction of any preceding embodiment, wherein the subject has an ischemic brain injury or has suffered an ischemic stroke, cardiac arrest, hemorrhagic shock, traumatic injury including brain injury, seizure activity, and/or epilepsy; or wherein the subject requires treatment for drug addiction, posttraumatic stress disorder, depression or other mental health conditions involving impaired or altered neural plasticity; or wherein sleep, sedative or anxiolytic effects are needed.

Disclosed herein are methods of enhancing the induction of any preceding embodiment, wherein the subject is conscious or not comatose.

Disclosed herein are methods of enhancing the induction of any preceding embodiment, wherein the $A_1AR$ agonist crosses the blood brain barrier.

Disclosed herein are methods of enhancing the induction of any preceding embodiment, wherein the $A_1AR$ agonist is $N^6$-cyclohexyladenosine (CHA) or capadenoson.

Disclosed herein are methods of enhancing the induction of any preceding embodiment, wherein the $A_1AR$ antagonist does not cross the blood-brain barrier.

Disclosed herein are methods of enhancing the induction of any preceding embodiment, wherein the $A_1AR$ antagonist is 8-p-sulfophenyltheophylline (8-SPT).

Disclosed herein are methods of enhancing the induction of any preceding embodiment, wherein if an $A_1AR$ agonist is administered, then an $A_1AR$ antagonist is also administered or the antagonist is titrated to minimize side effects of the agonist.

Disclosed herein are methods of enhancing the induction of any preceding embodiment, wherein the one or more $A_1AR$ agonists and the one or more $A_1AR$ antagonists are co-administered or the one or more antagonists are titrated to minimize side effects of the one or more agonists.

Disclosed herein are methods of enhancing the induction of any preceding embodiment, wherein the $A_1AR$ agonist is $N^6$-cyclohexyladenosine (CHA) or capadenoson and the $A_1AR$ antagonist is 8-p-sulfophenyltheophylline (8-SPT).

Disclosed herein are methods of enhancing the induction of any preceding embodiment, wherein the one or more $A_1AR$ agonists and one or more $A_1AR$ antagonists are administered to the subject intraperitoneally.

Disclosed herein are methods of enhancing the induction of any preceding embodiment, wherein the one or more $A_1AR$ agonists and one or more $A_1AR$ antagonists are administered to the subject intravenously, subcutaneously, intramuscularly, by cutaneous patch or orally.

Disclosed herein are methods of enhancing the induction of any preceding embodiment, further comprising maintaining hypothermia in the subject.

Disclosed herein are methods of enhancing the induction of any preceding embodiment, wherein maintaining hypothermia in the patient comprises repeating the administration of the one or more $A_1AR$ agonists and one or more $A_1AR$ antagonists.

Disclosed herein are methods of enhancing the induction of any preceding embodiment, wherein the subject is a non-human animal.

Disclosed herein are methods of enhancing the induction of any preceding embodiment, wherein the subject is a rat.

Disclosed herein are methods of enhancing the induction of any preceding embodiment, wherein the subject is an arctic ground squirrel.

Disclosed herein are compositions comprising one or more $A_1AR$ agonist, one or more $A_1AR$ antagonist, and a pharmaceutically acceptable carrier.

Disclosed herein are compositions of any preceding embodiment, wherein the $A_1AR$ agonist crosses the blood brain barrier.

Disclosed herein are compositions of any preceding embodiment, wherein the $A_1AR$ agonist is $N^6$-cyclohexyladenosine (CHA) or capadenoson.

Disclosed herein are compositions of any preceding embodiment, wherein the $A_1AR$ antagonist does not cross the blood-brain barrier.

Disclosed herein are compositions of any preceding embodiment, wherein the $A_1AR$ antagonist is 8-p-sulfophenyltheophylline (8-SPT).

Disclosed herein are compositions of any preceding embodiment, wherein the composition comprises $N^6$-cyclohexyladenosine (CHA) and 8-p-sulfophenyltheophylline (8-SPT).

Disclosed herein are compositions of any preceding embodiment, wherein the composition induces hypothermia in a subject.

Disclosed herein are methods of screening for a compound that induces therapeutic hypothermia in a subject comprising: determining the subject's body temperature; administering to the subject a candidate compound in combination with one or more of an $A_1AR$ agonist or one or more $A_1AR$ antagonist; determining the subject's body temperature following the administration of the $A_1AR$ agonist or $A_1AR$ antagonist, wherein a reduction in the subject's body temperature indicates that the candidate compound induces therapeutic hypothermia.

Disclosed herein are methods of screening any preceding embodiment, wherein the $A_1AR$ agonist crosses the blood brain barrier.

Disclosed herein are methods of screening any preceding embodiment, wherein the $A_1AR$ agonist is $N^6$-cyclohexyladenosine (CHA) or capadenoson.

Disclosed herein are methods of screening any preceding embodiment, wherein the $A_1AR$ antagonist does not cross the blood-brain barrier.

Disclosed herein are methods of screening any preceding embodiment, wherein the $A_1AR$ antagonist is 8-p-sulfophenyltheophylline (8-SPT).

Disclosed herein are methods of screening any preceding embodiment, wherein if an $A_1AR$ agonist is administered, then an $A_1AR$ antagonist is also administered or the antagonist is titrated to minimize side effects of the agonist.

Disclosed herein are methods of screening any preceding embodiment, wherein the one or more $A_1AR$ agonists or $A_1AR$ antagonists are administered to the subject intraperitoneally.

Also disclosed are the methods of screening any preceding embodiment, wherein the one or more $A_1AR$ agonists or $A_1AR$ antagonists are administered to the subject intravenously, subcutaneously, intramuscularly, by cutaneous patch or orally.

Disclosed herein are methods of screening any preceding embodiment, wherein the subject is a non-human animal.

Disclosed herein are methods of screening any preceding embodiment, wherein the subject is a rat.

Disclosed herein are methods of screening any preceding embodiment, wherein the subject is an arctic ground squirrel.

Disclosed herein are methods of treating ischemic brain injury in a subject comprising administering to the subject a therapeutically effective amount of one or more $A_1AR$ agonists and one or more $A_1AR$ antagonists.

Disclosed herein are methods of treating any preceding embodiment, wherein the ischemic brain injury comprises stroke, cardiac arrest, hemorrhagic shock, traumatic injury including brain injury, seizure activity, and/or epilepsy.

Disclosed herein are methods of treating any preceding embodiment, further comprising inducing therapeutic hypothermia in the subject.

Disclosed herein are methods of treating any preceding embodiment, further comprising maintaining hypothermia in the subject.

Disclosed herein are methods of treating any preceding embodiment, wherein maintaining hypothermia in the patient comprises repeating the administration of the one or more $A_1AR$ agonists and one or more $A_1AR$ antagonists.

Disclosed herein are methods of treating any preceding embodiment, wherein the subject is conscious or not comatose.

Disclosed herein are methods of treating any preceding embodiment, wherein the $A_1AR$ agonist crosses the blood brain barrier.

Disclosed herein are methods of treating any preceding embodiment, wherein the $A_1AR$ agonist is $N^6$-cyclohexyladenosine (CHA) or capadenoson.

Disclosed herein are methods of treating any preceding embodiment, wherein the $A_1AR$ antagonist does not cross the blood-brain barrier.

Disclosed herein are methods of treating any preceding embodiment, wherein the $A_1AR$ antagonist is 8-p-sulfophenyltheophylline (8-SPT).

Disclosed herein are methods of treating any preceding embodiment, wherein the one or more $A_1AR$ agonists and the one or more $A_1AR$ antagonists are co-administered or the antagonist is titrated to minimize side effects of the agonist.

Disclosed herein are methods of treating any preceding embodiment, wherein the $A_1AR$ agonist is $N^6$-cyclohexyladenosine (CHA) or capadenoson and the $A_1AR$ antagonist is 8-p-sulfophenyltheophylline (8-SPT).

Disclosed herein are methods of treating any preceding embodiment, wherein the one or more $A_1AR$ agonists or $A_1AR$ antagonists are administered to the subject intraperitoneally.

Disclosed herein are methods of treating any preceding embodiment, wherein the one or more $A_1AR$ agonists or $A_1AR$ antagonists are administered to the subject intravenously, subcutaneously, intramuscularly, by cutaneous patch or orally.

Disclosed herein are methods of identifying in a subject a neural region suitable for targeted therapy comprising: administering to the subject a therapeutically effective amount of one or more $A_1AR$ agonists; determining one or more neural regions that show a change in activation following administration of the one or more $A_1AR$ agonists, wherein a change in activation indicates a neural region suitable for targeted therapy, and wherein the targeted therapy induces therapeutic hypothermia in the subject.

Disclosed herein are methods of identifying any preceding embodiment, wherein the $A_1AR$ agonist crosses the blood brain barrier.

Disclosed herein are methods of identifying any preceding embodiment, wherein the $A_1AR$ agonist is $N^6$-cyclohexyladenosine (CHA) or capadenoson.

Disclosed herein are methods of identifying any preceding embodiment, wherein the activation of the one or more neural regions is determined by cFos immunochemistry.

Disclosed herein are methods of identifying any preceding embodiment, wherein the one or more $A_1AR$ agonists are administered in the winter or winter season.

Disclosed herein are methods of identifying any preceding embodiment, wherein the one or more $A_1AR$ agonists are administered in the summer or summer season.

Disclosed herein are methods of inducing torpor in a subject comprising administering to the subject a therapeutically effective amount of one or more $A_1AR$ agonists and one or more $A_1AR$ antagonists.

Disclosed herein are methods of inducing torpor of any preceding embodiment, wherein the $A_1AR$ agonist crosses the blood brain barrier.

Disclosed herein are methods of inducing torpor of any preceding embodiment, wherein the $A_1AR$ agonist is $N^6$-cyclohexyladenosine (CHA).

Disclosed herein are methods of inducing torpor of any preceding embodiment, wherein if an $A_1AR$ agonist is administered, then one or more of an $A_1AR$ antagonist is also administered.

Disclosed herein are methods of inducing torpor of any preceding embodiment, wherein the $A_1AR$ antagonist does not cross the blood-brain barrier.

Disclosed herein are methods of inducing torpor of any preceding embodiment, wherein the $A_1AR$ antagonist is 8-p-sulfophenyltheophylline (8-SPT).

Disclosed herein are methods of inducing torpor of any preceding embodiment, wherein the one or more $A_1AR$ agonists and the one or more $A_1AR$ antagonists are co-administered.

Disclosed herein are methods of inducing torpor of any preceding embodiment, wherein the $A_1AR$ agonist is $N^6$-cyclohexyladenosine (CHA) and the $A_1AR$ antagonist is 8-p-sulfophenyltheophylline (8-SPT).

Disclosed herein are methods of inducing torpor of any preceding embodiment, wherein the one or more $A_1AR$ agonists are administered to the subject intraperitoneally.

Disclosed herein are methods of inducing torpor of any preceding embodiment, wherein the one or more $A_1AR$ agonists are administered to the subject intravenously.

Disclosed herein are methods of inducing torpor of any preceding embodiment, wherein the subject is a non-human animal.

Disclosed herein are methods of inducing torpor of any preceding embodiment, wherein the subject is a rat.

Disclosed herein are methods of inducing torpor of any preceding embodiment, wherein the subject is an arctic ground squirrel.

These and other aspects of the disclosure are disclosed in more detail in the description of the invention given below.

BRIEF DESCRIPTION OF THE SEVERAL VIEWS OF THE DRAWINGS

The accompanying drawings, which are incorporated in and constitute a part of this specification, illustrate several embodiments and together with the description illustrate the disclosed compositions and methods.

FIG. 4A-FIG. 4C show that CHA at 16° C. Ta induced hypothermia, changed heart rates, and increased neurological deficits.

FIG. 7A-FIG. 7C show that 6 and 8 min asphyxiation produced similar decreases in hippocampal neuronal cell counts.

FIG. 8A-FIG. 8C show that rats in the therapeutic hypothermia group and the normothermic control group had similar mean arterial blood pressures before, during, and after induction of 8 min asphyxial cardiac arrest.

FIG. 10A-FIG. 10C show the average heart rate, systolic blood pressure, and diastolic blood pressure before, during, and after asphyxial cardiac arrest (8 min) in TH and NC groups.

FIG. 11A-FIG. 11C show heart rate, systolic blood pressure, and diastolic blood pressure before, during, and after induction of asphyxial cardiac arrest (6 or 8 min CA).

DETAILED DESCRIPTION OF THE INVENTION

Figure 1:
FIG. 1 shows a torpid arctic ground squirrel (AGS).

Before the present compounds, compositions, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations, it is specifically contemplated that each step comprises what is listed (unless that step includes a limiting term such as "consisting of"), meaning that each step is not intended to exclude, for example, other additives, components, integers or steps that are not listed in the step.

In this specification and in the claims that follow, reference will be made to a number of terms which shall be defined to have the following meanings:

"Optional" or "optionally" means that the subsequently described event or circumstance may or may not occur, and that the description includes instances where said event or circumstance occurs and instances where it does not.

In an aspect, "winter" or "winter season" can be defined by high torpor-inducing sensitivity to one or more $A_1AR$ agonist. For example, in an aspect, disclosed herein are methods comprising administering one or more $A_1AR$ agonists in winter or the winter season, as defined by high torpor-inducing sensitivity to one or more $A_1AR$ agonists.

In an aspect, "torpor" refers to a state of reduced physiological activity in an animal, usually characterized by reduced body temperature and metabolic rate.

In an aspect, "summer" or "summer season" can be defined by low torpor-inducing sensitivity to one or more $A_1AR$ agonist. For example, in an aspect, disclosed herein are methods comprising administering one or more $A_1AR$ agonists in summer or summer season, as defined by high torpor-inducing sensitivity to one or more $A_1AR$ agonist.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Compositions for Inducing Therapeutic Hypothermia

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular $A_1AR$ agonist or $A_1AR$ antagonist is disclosed and discussed and a number of modifications that can be made to a number of molecules including the $A_1AR$ agonist or $A_1AR$ antagonist are discussed, specifically contemplated is each and every combination and permutation of $A_1AR$ agonist or $A_1AR$ antagonist and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

In an aspect, disclosed herein are compositions comprising one or more adenosine or one or more adenosine analogs, adenosine receptor agonists, adenosine receptor antagonists, adenosine kinase inhibitors, or adenosine uptake inhibitors. Thus, in an aspect, disclosed herein are compositions comprising one or more adenosine receptor agonists such as, for example, an $A_1AR$ agonist.

As used herein, "adenosine" is a nucleoside composed of adenine attached to a ribose (ribofuranose) moiety via a β-N9-glycosidic bond having a structure represented by a formula:

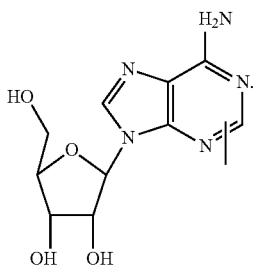

As used herein, an "adenosine analog" is any compound with a structure based on an adenosine and thus includes but is not limited to 5'-AMP, ADP, ATP, adenosine nucleotides, as well as other substituted adenosine compounds, insofar the substituted adenosine compounds are capable of being an adenosine receptor agonist.

The term "agonist" as used herein refers to a chemical structure capable of activating a receptor to induce a pharmacological response. Receptors can be activated or inactivated by either endogenous or exogenous agonists and antagonists, resulting in stimulating or inhibiting a biological response. A physiological agonist is a substance that creates the same or inhibiting a biological response. Typically, a physiological agonist creates the same bodily responses as does a natural ligand. A superagonist is an example of an agonist wherein the agonist produces a greater maximal response than the natural ligand for the target receptor, and thus an efficacy greater than 100%. This does not necessarily mean that it is more potent than the ligand, but is rather a comparison of the maximum possible response that can be produced inside a cell following receptor binding. Full agonists bind and activate a receptor, displaying full efficacy at that receptor. Partial agonists also bind and activate a given receptor, but have only partial efficacy at the receptor relative to a full agonist. An inverse agonist is an agent which binds to the same receptor binding-site as an agonist for that receptor and reverses constitutive activity of receptors. Inverse agonists exert the opposite pharmacological effect of a receptor agonist. An irreversible agonist is a type of agonist that binds permanently to a receptor in such a manner that the receptor is permanently activated. It is distinct from a mere agonist in that the association of an agonist to a receptor is reversible, whereas the binding of an irreversible agonist to a receptor is believed to be irreversible. This causes the compound to produce a brief burst of agonist activity, followed by desensitization and internalization of the receptor, which with long-term treatment produces an effect more like an antagonist. A selective agonist is specific for one certain type of receptor. In an aspect, disclosed herein are adenosine receptor agonists.

As used herein, an "$A_1$ adenosine receptor ($A_1AR$) agonist" is any compound capable of having an agonizing effect on the $A_1$ adenosine receptor ($A_1AR$). Thus, in an aspect, disclosed herein are compositions comprising one or more selective or nonselective $A_1AR$ agonists (such as, for example, $N^6$-cyclohexyladenosine (CHA) or capadenoson, including a composition comprising both CHA and capadenoson).

$N^6$-cyclohexyladenosine (CHA) is an $A_1AR$ agonist having a structure represented by a formula:

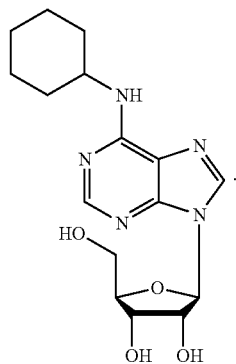

Capadenoson (also known as BAY-68-4986) is an $A_1AR$ agonist having a structure represented by a formula:

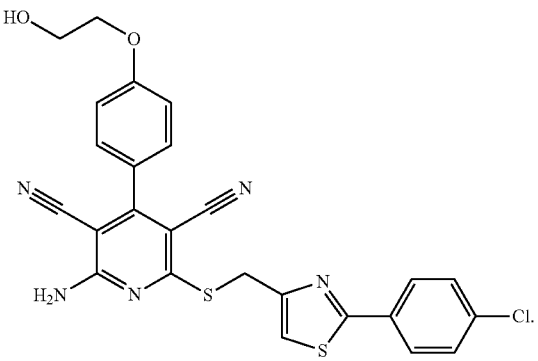 [SMILES: N#Cc1c(N)nc(SCc2csc(-c3ccc(Cl)cc3)n2)c(C#N)c1-c1ccc(OCCO)cc1]

Other $A_1AR$ agonists include, but are not limited to, the following: Selodenoson (DTI-0009), GR79236 (Glaxo), SDZ-WAG-994 (Novartis), GW493838 (GlaxoSmithKline), PJ-875 (AF from Inotek), GR79236, ARA, CVT-3619, $N^6$-cyclopentyl adenosine (CPA), adenosine monophosphate (AMP) (Rittiner et al., 2012), 2-chloro-$N^6$-cyclopentyladenosine (CCPA), R—$N^6$-phenylisopropyladenosine (S-PIA), S—$N^6$-phenylisopropyladenosine (S-PIA), 5'-N-ethylcarboxamidoadenosine (NECA), $N^6$-3-iodobenzyladenosine-5'-N-methyluronamide (IB-MECA), N⁶-4-amino-3-iodobenzyladenosine-5'-N-methyluronamide (IAB-MECA), and ((2R,3S,4R,5R)-5-(6-(Cyclopentylamino)-9H-purin-9-yl)-3,4-dihydroxytetrahydrofuran-2-yl)methyl Dimethyl Phosphate (i.e., Compound 5a described in Korboukh et al., 2012).

In an aspect, the compositions disclosed herein can comprise an adenosine receptor antagonist such as, for example, an $A_1AR$ antagonist. The term "antagonist" as used herein refers to a substance that interferes with the effects of another substance. Functional or physiological antagonism occurs when two substances produce opposite effects on the same physiological function. Chemical antagonism or inactivation is a reaction between two substances to neutralize their effects. Dispositional antagonism is the alternation of the disposition of a substance (its absorption, biotransformation, distribution, or excretion) so that less of the agent reaches the target or its persistence there is reduced. Antagonism at the receptor for a substance entails the blockade of the effect of an agonist with an appropriate antagonist that competes for the same site. As used herein, an $A_1AR$ antagonist can refer to any compound capable of having an antagonizing effect on the $A_1AR$. Thus, in an aspect, disclosed herein are compositions comprising one or more selective or nonselective $A_1AR$ antagonists (such as, for example, 8-p-sulfophenyltheophylline (8-SPT).

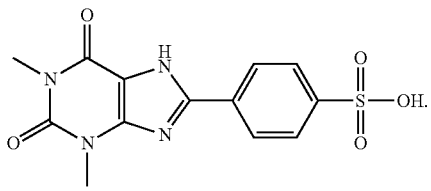 [SMILES: Cn1c(=O)c2[nH]c(-c3ccc(S(=O)(=O)O)cc3)nc2n(C)c1=O]

It is understood and herein contemplated that the disclosed compositions can comprise both agonists and antagonists. Thus, in an aspect disclosed herein are compositions comprising one or more $A_1AR$ agonists (such as, for example CHA and/or capadenoson) and one or more $A_1AR$ antagonists (such as, for example, 8-SPT). For example, disclosed herein are compositions comprising CHA and 8-SPT; or capadenoson and 8-SPT; or CHA, capadenoson, and 8-SPT.

It is understood that the adenosine receptor agonists disclosed herein can have deleterious side effects in the subject. Accordingly, disclosed herein are compositions where one or more $A_1AR$ antagonists can be titrated to minimize side effects of one or more $A_1AR$ agonists.

In an aspect, the disclosed compositions can further comprise additional agents such as cyclodextrins. For example, hydroxypropyl-β-cyclodextrin increases the solubility and stability of CHA in solution without compromising distribution into the CNS. Thus, in an aspect, disclosed herein are compositions comprising one or more $A_1AR$ agonists (for example CHA and/or capadenoson) and/or one or more $A_1AR$ antagonists (for example, 8-SPT) and further comprising cyclodextrin. For example, disclosed herein are compositions comprising CHA and hydroxypropyl-β-cyclodextrin; or capadenoson and cyclodextrin; or 8-SPT and cyclodextrin; CHA, 8-SPT, and cyclodextrin; or capadenoson, 8-SPT, and cyclodextrin; or CHA, capadenoson, 8-SPT, and cyclodextrin. The skilled person is familiar with cyclodextrins, which include but are not limited to: α (alpha)-cyclodextrins (6-membered sugar ring molecule), β (beta)-cyclodextrins (7-membered sugar ring molecule), and γ (gamma)-cyclodextrins (8-membered sugar ring molecule).

In an aspect, disclosed herein are compositions comprising one or more $A_1AR$ agonists (for example, CHA and/or capadenoson) and/or one or more $A_1AR$ antagonists (for example, 8-SPT) and further comprising polyethelyene glycol-400 (PEG-400). For example, disclosed herein are compositions comprising CHA and PEG-400; or capadenoson and PEG-400; or 8-SPT and PEG-400; or CHA, 8-SPT, and PEG-400; or capadenoson, 8-SPT, and PEG-400; or CHA, capadenoson, 8-SPT, and PEG-400.

In an aspect, disclosed herein are compositions comprising one or more $A_1AR$ agonists (for example CHA and/or capadenoson) and/or one or more $A_1AR$ antagonists (for example, 8-SPT) and further comprising glycerol. For example, disclosed herein are compositions comprising CHA and glycerol; or capadenoson and glycerol; or 8-SPT and glycerol; or CHA, 8-SPT, and glycerol; or capadenoson, 8-SPT, and glycerol; or CHA, capadenoson, 8-SPT, and glycerol.

It is understood that the pharmaceutical formulation or delivery of the disclosed compositions (e.g., the compositions comprising one or more $A_1AR$ agonists and/or one or more $A_1AR$ antagonist) may be enhanced by the presence of a pharmaceutically acceptable carrier. Thus, in an aspect, disclosed herein is a composition comprising one or more $A_1AR$ agonist, one or more $A_1AR$ antagonist, and a pharmaceutically acceptable carrier.

It is understood and herein contemplated that depending on the $A_1AR$ agonist used in the composition, the agonist may be able to cross the blood brain barrier. The ability to cross the blood brain barrier is significant as said ability allows for access to sites of action within the central nervous system. In the central nervous system (CNS), $A_1AR$ agonists can disinhibit neural circuits to induce onset of torpor (Jinka et al., 2011). A benefit of disinhibiting these circuits is suppression of shivering and nonshivering thermogenesis and a decrease in body temperature. While these effects of the $A_1AR$ agonist result from activation of $A_1AR$ within the CNS, $A_1AR$ agonists acting outside of the CNS produce life-threatening side-effects including bradycardia and paralysis of the heart. These side-effects can be avoided by blocking $A_1AR$ with an antagonist. An $A_1AR$ antagonist that does not cross the blood brain barrier blocks the effects of the $A_1AR$ agonist on the heart and other tissues that lie outside of the blood brain barrier without interfering with the torpor-inducing effects of the $A_1AR$ agonist. Thus, in an aspect, disclosed herein are compositions comprising one or more $A_1AR$ agonist and/or one or more $A_1AR$ antagonist, wherein the one or more $A_1AR$ agonist crosses the blood brain barrier. For example, a composition comprising CHA and/or capadenoson. In an aspect, disclosed herein are compositions comprising one or more $A_1AR$ agonist and/or one or more $A_1AR$ antagonist, wherein the one or more $A_1AR$ antagonist does not cross the blood-brain barrier. For example a composition comprising 8-SPT. It is understood that it can be advantageous to have one or more $A_1AR$ agonist that crosses the blood brain barrier and one or more $A_1AR$ antagonist in the same composition. Therefore, disclosed herein are compositions comprising one or more $A_1AR$ agonists and one or more $A_1AR$ antagonists, wherein the one or more $A_1AR$ agonist crosses the blood brain barrier and one or more $A_1AR$ antagonist does not cross the blood-brain barrier.

Disclosed herein are pharmaceutical compositions comprising one or more of the disclosed compounds. For example, disclosed herein is a pharmaceutical composition comprising one or more $A_1AR$ agonists and one or more $A_1AR$ antagonists. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case depends on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, dimethyl sulfoxide (DMSO) and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case depends on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, dimethyl sulfoxide (DMSO) and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. For example, in an aspect, a cream or ointment can be prepared by mixing a hydrophilic material and water, together with about 5 wt % to about 10 wt % of the compound, to produce a cream or ointment having a desired consistency. In an aspect, a cream or ointment can be prepared by mixing a hydrophobic material and DMSO, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions that require negative allosteric modulation of adenosine receptor activity, an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient depends upon a variety of factors. Such factors include the age, body weight, general health, sex, and diet of the patient. Other factors include the time and route of administration, rate of excretion, drug combination, and the type and severity of the particular disease undergoing therapy.

The present disclosure is further directed to methods for the manufacture of a medicament for modulating adenosine receptor activity (e.g., treatment of one or more neurological and/or psychiatric disorder associated with adenosine dysfunction) in mammals (e.g., humans) comprising combining one or more disclosed compounds, products, or compositions with a pharmaceutically acceptable carrier or diluent. Thus, in an aspect, the disclosure relates to methods for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the pathological conditions disclosed herein. As disclosed herein, it is understood that the compositions disclosed herein can be used for the treatment or prevention of a pathological condition such as, for example ischemic brain injury, cardiac arrest, hemorrhagic shock, traumatic injury including brain injury, seizure activity, and/or epilepsy; or wherein the subject requires treatment for drug addiction, post-traumatic stress disorder, depression or other mental health conditions involving impaired or altered neural plasticity; or conditions wherein sleep, sedative or anxiolytic effects are needed. As disclosed herein, one or more of the above-identified diseases, disorders, or conditions can be affected by suboptimal adenosine signaling. Thus, a subject having one or more of the above-identified diseases, disorders, or conditions can benefit from adenosine receptor activation, or can respond to neuronal remodeling induced by cooling and rewarming. It is further understood that the disclosed compositions can be used to induce torpor or hypothermia, including but not limited to therapeutic hypothermia.

Method of Inducing Therapeutic Hypothermia and/or Torpor

Disclosed herein are methods of inducing therapeutic hypothermia in a subject comprising administering to the subject any of the compositions disclosed herein. Hypothermia generally refers to the lowering of the core temperature of the body below normal level. Normal body temperature in an adult human measured rectally over 24 hours is 37° C.+/−0.6° C. and is thus variable between individuals, and over time within the individual. Hypothermia as a medical condition is usually defined as the effects seen on the body once the core temperature drops below 35° C. It may become critical, if the body temperature falls below 32° C. As used herein, hypothermia is defined as the lowering of body temperature, preferably to below normal levels. Therapeutic hypothermia refers to a medical treatment that lowers a patient's body temperature in order to help reduce the risk of ischemic injury to tissue following a period of insufficient blood flow.

It is understood and herein contemplated that the disclosed therapeutic hypothermia can be induced through the administration of a composition. In an aspect, the present disclosure relates to methods of inducing therapeutic hypothermia in a subject comprising administering to the subject a therapeutically effective amount of adenosine or one or more adenosine analogs, adenosine receptor agonists, adenosine receptor antagonists, adenosine kinase inhibitors, or adenosine uptake inhibitors.

In an aspect, the present disclosure relates to methods of inducing therapeutic hypothermia in a subject comprising administering to the subject a therapeutically effective amount of one or more $A_1AR$ agonists or a composition comprising the same. In an aspect, the one or more $A_1AR$ agonist can be any $A_1AR$ agonist disclosed herein. For example, disclosed herein are methods of inducing therapeutic hypothermia in a subject comprising administering to the subject one or more $A_1AR$ agonists wherein at least one of the $A_1AR$ agonist is $N^6$-cyclohexyladenosine (CHA) and/or capadenoson.

In an aspect, the present disclosure relates to methods of inducing therapeutic hypothermia in a subject comprising administering to the subject a therapeutically effective amount of one or more adenosine $A_1$ receptor ($A_1AR$) antagonists (such as, for example, 8-p-sulfophenyltheophylline (8-SPT)). In an aspect, the present disclosure relates to methods of inducing therapeutic hypothermia in a subject comprising administering to the subject a therapeutically effective amount of one or more $A_1AR$ antagonists, wherein at least one of the one or more $A_1AR$ antagonists is 8-p-sulfophenyltheophylline (8-SPT).

In an aspect, the present disclosure relates to methods of inducing therapeutic hypothermia in a subject comprising administering to the subject a therapeutically effective amount of one or more adenosine $A_1$ receptor ($A_1AR$) agonists (such as, for example, CHA or capadenoson) and/or one or more adenosine $A_1$ receptor ($A_1AR$) antagonists (such as, for example, 8-SPT). In an aspect, the present disclosure relates to methods of inducing therapeutic hypothermia in a subject comprising administering to the subject a therapeutically effective amount of one or more adenosine $A_1$ receptor ($A_1AR$) agonists and one or more adenosine $A_1$ receptor ($A_1AR$) antagonists wherein the $A_1AR$ agonist is $N^6$-cyclohexyladenosine (CHA) or capadenoson and the $A_1AR$ antagonist is 8-p-sulfophenyltheophylline (8-SPT).

It is understood and herein contemplated that in additional compositions or components to a single composition can be administered with the disclosed agonists and antagonists to induce therapeutic hypothermia. Thus, in an aspect, disclosed herein are methods of inducing therapeutic hypothermia in a subject comprising administering to the subject a therapeutically effective amount of one or more adenosine $A_1$ receptor ($A_1AR$) agonists and one or more adenosine $A_1$ receptor ($A_1AR$) antagonists, further comprising administering to the subject cyclodextrin.

In an aspect, the present disclosure relates to methods of inducing therapeutic hypothermia in a subject comprising administering to the subject a therapeutically effective amount of one or more adenosine $A_1$ receptor ($A_1AR$) agonists and one or more adenosine $A_1$ receptor ($A_1AR$) antagonists wherein the one or more $A_1AR$ agonists and the one or more $A_1AR$ antagonists are co-administered or the antagonist is titrated to minimize side effects of the agonist.

In an aspect, the disclosed methods of inducing therapeutic hypothermia can be used as a treatment for a disease or condition such as, for example, ischemic brain injury. Thus, in an aspect disclosed herein are methods of inducing therapeutic hympothermia in a subject wherein the subject has an ischemic brain injury or has suffered an ischemic stroke, cardiac arrest, hemorrhagic shock, traumatic injury including brain injury, seizure activity, and/or epilepsy; or wherein the subject requires treatment for drug addiction, post-traumatic stress disorder, depression or other mental health conditions involving impaired or altered neural plasticity; or wherein sleep, sedative or anxiolytic effects are needed.

Ischemia is the reduction or abolition of blood supply to a tissue. The associated deficiency of oxygen and nutrients may lead to cell death (necrosis) in areas of the affected tissue. The damage induced by the lack of oxygenated blood in the brain occurs in two stages. First, cellular metabolism is arrested due to lack of oxygen and some cells and tissue die within minutes as a consequence thereof. Second, cascades of processes such as apoptosis are initiated and continue up to 12 hours after the event that initially induced the ischemic state has been abolished. The tissue damaged by the second cascade can be crucial and cause greater harm to the individual than the primary damage happening with the first minutes of ischemia. In an aspect, the present disclosure is aimed at correcting ischemia of the brain thereby minimizing damage to the central nervous system.

The neuroprotective efficacy of induced hypothermia following or during ischemia of the brain is evident in experimental animal models of stroke. In humans, two trials conducted in cardiac arrest patients have shown improved neurological outcome of inducing hypothermia. The therapeutic hypothermia did not increase the complication rate in these two trials and the use of induced hypothermia in comatose survivors of cardiac arrest is now recommended internationally. Hypothermia counteracts ischemic brain damage by several mechanisms. For example, ischemia induces opening of the blood-brain barrier, a process that seems to be very sensitive to brain temperature. This is evident from studies of tracers and their migration across the blood-brain barrier, in which hypothermia attenuates extravasation several hours after ischemia and prevents vasogenic oedema. Reperfusion after brain ischemia results in the production of free radicals, which causes peroxidation and destruction of membrane lipids. Hypothermia prevents the production of free radicals such as hydroxyl and nitric oxide during reperfusion after brain ischemia.

Amino acids, such as glutamate, aspartate, and glycine, act as excitotoxic neurotransmitters by over stimulation of neurons in the vicinity of ischemic damage, which causes further injury. Hypothermia lowers the release and can even cause a more rapid reuptake of these transmitters. Release of excitotoxic neurotransmitters can also cause progressive neuronal death in the penumbra in stroke patients, and hypothermia after cerebral ischemia can attenuate this process.

During ischemia, cellular metabolism in the penumbra undergoes significant changes. As the neurons continue to fire, potassium ions flood into the extra-cellular space, calcium ions flow into the neurons leading to cytoskeletal degradation, and ATP concentrations fall as energy depletion continues. Hypothermia reduces calcium influx and the subsequent breakdown of intracellular structures, improves potassium ion homoeostasis, and helps metabolic functions such as calcium or calmodulin-dependent protein kinase activity to recover. By lowering of neutrophil and microglial activation after ischemia, hypothermia also has an anti-inflammatory effect.

Apoptosis and DNA changes are crucial stages in delayed neuronal death after transient cerebral ischemia. Hypothermia directly inhibits apoptosis and can also increase endogenous production of the anti-apoptotic protein Bcl2. Hypothermia can even have effects at the DNA level: A slight lowering of brain temperature results in less DNA fragmentation and less apoptosis.

Induction of hypothermia by lowering of the core temperature of the body has been attempted by mechanical cooling devices such as surface cooling and cooling using catheters placed in a large vessel. However, these mechanical inducers of hypothermia have been shown to have considerable unwanted side effects. These side effects include shivering, serious infections and lung puncture. Shivering causes an increased exertion of the heart of the patient, and in some cases, this results in ischemia of the heart and hereby increased morbidity and mortality.

The regulation of the core temperature of the body by a pharmaceutical composition comprising a one or more compounds capable of inducing hypothermia does not only solve the problem of reducing or preventing the effects of ischemia, such as tissue damaging effects, but is also relevant as a safer and less expensive alternative to the currently employed mechanical methods.

Knowledge of the molecular and physiological mechanisms used by the arctic ground squirrel (AGS) to suppress shivering during onset of hibernation can translate into improved strategies to defeat the thermoregulatory defenses that normally complicate induction and maintenance of therapeutic hypothermia. By suppressing shivering and non-shivering thermogenesis during onset of torpor, hibernating mammals can reduce their levels of oxygen consumption to as low as 2% of basal metabolic rate (Buck and Barnes, 2000; Geiser, 1988). In small mammals (<5 kg) Tb gradually approaches ambient temperature as hibernating animals enter torpor. Core Tb in hibernating ground squirrels can fall to as low as −3° C. (Barnes, 1989), and even in larger, thermally insulated species such as the black bear core Tb can decrease to as low as 29° C. (Toien et al., 2011). Study of natural hibernation revealed two important principles relevant to therapeutic hypothermia. First, shivering is alleviated through stimulation of central $A_1AR$. Data provided herein shows that repeated co-administration of CHA (an $A_1AR$ agonist that readily penetrates the blood brain barrier) and 8-p-sulfophenyltheophylline (8-SPT, a peripherally acting $A_1AR$ antagonist) produces an immediate decrease in $T_b$ in conscious rats. Cooling is sustained and enhanced by repeated drug administration. The magnitude of cooling at a given dose of CHA is enhanced following restricted diet (DR) where the response to CHA and 8-SPT resembles torpor in rate of cooling and in the way that Tb approaches ambient temperature. Accordingly disclosed herein are methods of inducing torpor in a subject.

In an aspect, the disclosed methods of inducing torpor in a subject comprising administering to the subject a therapeutically effective amount of one or more $A_1AR$ agonists (such as, for example CHA and/or capadenoson) and/or one or more $A_1AR$ antagonists (such as, for example, 8-SPT). For example, disclosed herein are methods of inducing torpor comprising administering to the subject a therapeutically effective amount of one or more $A_1AR$ agonists and one or more $A_1AR$ antagonists, wherein the $A_1AR$ agonist is $N^6$-cyclohexyladenosine (CHA) and the $A_1AR$ antagonist is 8-p-sulfophenyltheophylline (8-SPT).

It is understood and herein contemplated that in additional compositions or components to a single composition can be administered with the disclosed agonists and antagonists to induce torpor. Thus, in an aspect, disclosed herein are methods of inducing torpor in a subject comprising administering to the subject a therapeutically effective amount of one or more adenosine $A_1$ receptor ($A_1AR$) agonists and one or more adenosine $A_1$ receptor ($A_1AR$) antagonists, further comprising administering to the subject cyclodextrin.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In an aspect, the subject is a mammal. A patient refers to a subject afflicted with a disease or disorder. The term "patient" includes human and veterinary subjects. In an aspect of the disclosed methods, the subject has been diagnosed with a need for treatment of one or more disorder or injury associated with ischemic tissue damage prior to the administering step.

In an aspect, disclosed herein are methods of inducing therapeutic hypothermia and/or torpor in a subject that is conscious, unconscious, comatose, or not comatose.

In an aspect, disclosed herein are methods of inducing therapeutic hypothermia and/or torpor in a subject comprising administering to the subject a therapeutically effective amount of one or more $A_1AR$ agonist wherein the $A_1AR$ agonist crosses the blood brain barrier.

In an aspect, disclosed herein are methods of inducing therapeutic hypothermia and/or torpor in a subject comprising administering to the subject a therapeutically effective amount of one or more $A_1AR$ antagonist wherein the $A_1AR$ antagonist does not cross the blood-brain barrier.

In an aspect, the present disclosure relates to methods of inducing therapeutic hypothermia and/or torpor in a subject comprising administering to the subject a therapeutically effective amount of one or more adenosine $A_1$ receptor ($A_1AR$) agonists.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intraplural administration, intraperitoneal administration, intramuscular administration, and subcutaneous administration. Administration can occur as a single dose or as multiple doses. Administration can be continuous or intermittent. In various aspects, a preparation can be administered therapeutically; that is, administered to treat an existing disease or condition. In further various aspects, a preparation can be administered prophylactically; that is, administered for prevention of a disease or condition. Thus, in an aspect, the present disclosure relates to methods of inducing therapeutic hypothermia and/or torpor in a subject comprising administering to the subject a therapeutically effective amount of one or more adenosine $A_1$ receptor ($A_1AR$) agonists and one or more adenosine $A_1$ receptor ($A_1AR$) antagonists wherein the one or more $A_1AR$ agonists or $A_1AR$ antagonists are administered to the subject intraperitoneally, intravenously, subcutaneously, intramuscularly, by cutaneous patch, or orally.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result (e.g., hypothermia and/or torpor in a subject) or to have an effect on undesired symptoms, but is generally insufficient to cause adverse side effects. The specific therapeutically effective dose level for any particular patient depends upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

In an aspect, the present disclosure relates to methods of inducing therapeutic hypothermia in a subject comprising administering to the subject a therapeutically effective amount of one or more adenosine $A_1$ receptor ($A_1AR$) agonists and one or more adenosine $A_1$ receptor ($A_1AR$) antagonists and further comprising maintaining hypothermia in the subject.

In an aspect, the present disclosure relates to methods of inducing therapeutic hypothermia in a subject comprising administering to the subject a therapeutically effective amount of one or more adenosine $A_1$ receptor ($A_1AR$) agonists and one or more adenosine $A_1$ receptor ($A_1AR$) antagonists, wherein maintaining hypothermia in the subject comprises repeating the administration of the one or more $A_1AR$ agonists or $A_1AR$ antagonists.

Method of Enhancing the Induction of Therapeutic Hypothermia

It is understood and herein contemplated that the disclosed methods of inducing therapeutic hypothermia and/or torpor can be used in conjunction with other physical (restrictive diet, external cooling, etc) or pharmacological methods of inducing therapeutic hypothermia. That is, in an aspect, the present disclosure relates to methods of enhancing the induction of therapeutic hypothermia in a subject.

Thus, disclosed herein are methods of enhancing the induction of therapeutic hypothermia in a subject comprising administering to the subject a therapeutically effective amount of one or more $A_1AR$ agonists (such as, for example CHA and/or capadenoson) and/or one or more $A_1AR$ antagonists (such as, for example, 8-SPT). For example, disclosed herein are methods of enhancing the induction of therapeutic hypothermia comprising administering to the subject a therapeutically effective amount of one or more $A_1AR$ agonists and one or more $A_1AR$ antagonists, wherein the $A_1AR$ agonist is $N^6$-cyclohexyladenosine (CHA) and the $A_1AR$ antagonist is 8-p-sulfophenyltheophylline (8-SPT).

It is understood and herein contemplated that in additional compositions or components to a single composition can be administered with the disclosed agonists and antagonists to enhance the induction therapeutic hypothermia. Thus, in an aspect disclosed herein are methods of enhancing the induction of therapeutic hypothermia in a subject comprising administering to the subject a therapeutically effective amount of one or more adenosine $A_1$ receptor ($A_1AR$) agonists and one or more adenosine $A_1$ receptor ($A_1AR$) antagonists, further comprising administering to the subject cyclodextrin.

In an aspect, the present disclosure relates to methods of enhancing the induction of therapeutic hypothermia in a subject comprising administering to the subject a therapeutically effective amount of one or more $A_1AR$ agonists, wherein the subject is fed a restrictive diet for a predetermined time period prior to the administration of the one or more $A_1AR$ agonists and/or one or more $A_1AR$ antagonists. In an aspect, the present disclosure relates to methods of enhancing the induction of therapeutic hypothermia in a subject comprising administering to the subject a therapeutically effective amount of one or more $A_1AR$ antagonists, wherein the subject is fed a restrictive diet for a predetermined time period prior to the administration of the one or more $A_1AR$ antagonists. In an aspect, the present disclosure relates to methods of enhancing the induction of therapeutic hypothermia in a subject wherein the subject is fed every other day. In an aspect, the one or more $A_1AR$ antagonists can be administered with one or more $A_1AR$ agonists.

In an aspect, the present disclosure relates to methods of enhancing the induction of therapeutic hypothermia in a subject, wherein the subject has an ischemic brain injury or has suffered an ischemic stroke, cardiac arrest, hemorrhagic shock, traumatic injury including brain injury, seizure activity, and/or epilepsy; or wherein the subject requires treatment for drug addiction, post-traumatic stress disorder, depression or other mental health conditions involving impaired or altered neural plasticity; or wherein sleep, sedative or anxiolytic effects are needed.

In an aspect, the present disclosure relates to methods of enhancing the induction of therapeutic hypothermia in a subject, wherein the subject is conscious, unconscious, comatose or not comatose.

In an aspect, the present disclosure relates to methods of enhancing the induction of therapeutic hypothermia in a subject, further comprising maintaining hypothermia in the subject.

Disclosed herein are methods of enhancing the induction of therapeutic hypothermia in a subject, comprising maintaining hypothermia in a subject, wherein maintaining hypothermia in the subject comprises administering a single dose of one or more disclosed $A_1AR$ agonists.

Disclosed herein are methods of enhancing the induction of therapeutic hypothermia in a subject, comprising maintaining hypothermia in a subject, wherein maintaining hypothermia in the subject comprises administering a single dose of one or more disclosed $A_1AR$ agonists and one or more disclosed $A_1AR$ antagonists.

In an aspect, the present disclosure relates to methods of enhancing the induction of therapeutic hypothermia in a subject, wherein maintaining hypothermia in the patient comprises repeating the administration of the one or more $A_1AR$ agonists and one or more $A_1AR$ antagonists.

Method of Treating Ischemic Brain Injury

In an aspect, the disclosed methods of inducing therapeutic hypothermia can be used to treat a subject suffering from ischemic brain injury, ischemic stroke, cardiac arrest, hemorrhagic shock, traumatic injury including brain injury, seizure activity, and/or epilepsy; or wherein the subject requires treatment for drug addiction, post-traumatic stress disorder, depression or other mental health conditions involving impaired or altered neural plasticity; or wherein sleep, sedative or anxiolytic effects are needed. Thus, in an aspect, disclosed herein are methods of treating ischemic brain injury in a subject.

As used herein, the term "treating" or "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In an aspect, the subject is a mammal such as a primate, including non-human primates, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

In an aspect, disclosed herein are methods of treating ischemic brain injury in a subject comprising administering to the subject a therapeutically effective amount of one or more $A_1AR$ agonists and/or a therapeutically effective amount of one or more $A_1AR$ antagonists. It is understood and herein contemplated that the disclosed methods of treatment can treat ischemic brain injury by administering the disclosed agonists and antagonists which can have the therapeutic effect of inducing therapeutic hypothermia while mitigating the side-effects of stimulating $A_1AR$ outside of the CNS. Therefore, in an aspect, disclosed herein are methods of treating ischemic brain injury, further comprising inducing therapeutic hypothermia in the subject. In some instances it can be beneficial to maintain the therapeutic hypothermia. Accordingly, in an aspect, discloses herein are methods of treating ischemic brain injury, further comprising maintaining hypothermia in the subject.

As noted above, therapeutic hypothermia can be induced through the administration of one or more $A_1AR$ agonists (such as, for example, $N^6$-cyclohexyladenosine (CHA) or capadenoson) and/or one or more $A_1AR$ antagonists (such as, for example, 8-SPT). As inducing therapeutic hypothermia has a therapeutic effect on ischemic brain injury, in an aspect, disclosed herein are methods of treating ischemic brain injury in a subject comprising administering to the subject one or more $A_1AR$ agonists (such as, for example, $N^6$-cyclohexyladenosine (CHA) or capadenoson) and/or one $A_1AR$ antagonists (such as, for example, 8-SPT). Thus, it is understood that in an aspect, disclosed herein are methods of treating ischemic brain injury in a subject comprising administering to the subject one or more $A_1AR$ agonists (such as, for example CHA or capadenoson). Also disclosed herein are methods of treating ischemic brain injury in a subject comprising administering to the subject one or more $A_1AR$ antagonists (such as, for example 8-SPT). In an aspect, disclosed herein are methods of treating ischemic brain injury in a subject comprising administering to the subject one or more $A_1AR$ agonists (such as, for example, CHA and/or capadenoson) and one or more A1AR antagonists (such as, for example, 8-SPT). In an aspect, the method of treating ischemic injury can further comprise administering to the subject cyclodextrin.

Treatment of ischemic brain injury can occur through administration of the $A_1AR$ agonist and/or one or more $A_1AR$ antagonists in a single dose administration, concurrent administration, co-administration, or sequential administration. Therefore, administration can occur at the same time, within 1, 2, 3, 4, 5, 6, 7, 8, 9, 10, 11, 12, 13, 14, 15, 20, 25, 30, 35, 40, 45, 50, 55, 60 minutes, 2, 3, 4, 5, 6, 7, 8, 9, 10, 11, 12, 13, 14, 15, 16, 17, 18, 19, 20, 21, 22, 23, 24, 36, 48, 60, 72, 84, or 96 hours. Administration can occur in any order. For example, the agonist can be administered before, at the same time, or after any additional agonist and/or any antagonist. It is understood and herein contemplated that in some aspects, it can be advantageous to maintain or stabilize the hypothermic state of the subject for periods longer than can be accomplished through single administration of the one or more $A_1AR$ agonist and/or one or more $A_1AR$ antagonist. Thus, in an aspect disclosed herein are methods of treating ischemic brain injury, wherein maintaining hypothermia in the patient comprises repeating the administration of the one or more $A_1AR$ agonists and/or antagonists.

The disclosed $A_1AR$ agonist and/or one or more $A_1AR$ antagonist can be administered by any route appropriate for administration of a composition. For example, in an aspect, disclosed herein are methods of treating ischemic brain injury, wherein the one or more $A_1AR$ agonists or $A_1AR$ antagonists are administered to the subject intraperitoneally, for example, the one or more $A_1AR$ agonists or $A_1AR$ antagonists can be administered to the subject intravenously, subcutaneously, or intramuscularly. Additionally, the $A_1AR$ agonists or $A_1AR$ antagonists can be administered to the subject by cutaneous patch or orally.

It is understood that the disclosed treatment methods are appropriate regardless of the state of responsiveness of the subject to external stimuli. In an aspect the subject can be conscious, unconscious, comatose, or not comatose.

In an aspect, disclosed herein are methods of treating ischemic brain injury, wherein the antagonist is titrated to minimize side effects of the agonist.

Method of Screening for a Compound that Induces Therapeutic Hypothermia

It is understood that given the effect of $A_1AR$ agonists and $A_1AR$ antagonists on inducing therapeutic hypothermia in a subject, it is advantageous to discover new $A_1AR$ agonists and $A_1AR$ antagonists. Thus, in an aspect, disclosed herein are methods of screening for a compound that induces therapeutic hypothermia in a subject. For example, disclosed herein are methods of screening for a compound that induces therapeutic hypothermia in a subject comprising: (i) determining the subject's body temperature; (ii) administering to the subject a candidate compound in combination with one or more of an $A_1AR$ agonist (such as, for example, CHA or capadenoson—also known as BAY-68-4986) and/or one or more $A_1AR$ antagonist (such as, for example, 8-SPT); (iii) determining the subject's body temperature following the administration of the $A_1AR$ agonist or $A_1AR$ antagonist, wherein a reduction in the subject's body temperature indicates that the candidate compound induces therapeutic hypothermia.

In an aspect, disclosed herein are methods of screening for a compound that induces therapeutic hypothermia in a subject, wherein if an $A_1AR$ agonist is administered, then an $A_1AR$ antagonist is also administered or the antagonist is titrated to minimize side effects of the agonist. In an aspect, the one or more $A_1AR$ agonists or $A_1AR$ antagonists can be administered to the subject intraperitoneally, intravenously, subcutaneously, intramuscularly, by cutaneous patch or orally.

In an aspect, disclosed herein are methods of screening for a candidate compound that induces therapeutic hypothermia in a subject, wherein the $A_1AR$ agonist crosses the blood brain barrier and/or the $A_1AR$ antagonist does not cross the blood-brain barrier.

Method of Identifying Neural Regions for Targeting Therapy

The disclosed methods used compositions in the form of $A_1AR$ agonists and $A_1AR$ antagonist to induce torpor, induce therapeutic hypothermia, enhance therapeutic hypothermia, and/or treat ischemic brain injury. It is understood that such $A_1AR$ agonists and $A_1AR$ antagonist act by activating or shutting down neural pathways. Therefore, it is advantageous to identify new neural regions suitable for targeted therapy. Accordingly, the present disclosure comprises methods of identifying in a subject a neural region suitable for targeted therapy. In an aspect, disclosed herein are methods of identifying in a subject a neural region suitable for targeted therapy comprising: (i) administering to the subject a therapeutically effective amount of one or more $A_1AR$ agonists (such as, for example CHA and/or capadenoson); (ii) determining one or more neural regions that show a change in activation following administration of the one or more $A_1AR$ agonists, wherein a change in activation indicates a neural region suitable for targeted therapy, and wherein the targeted therapy induces therapeutic hypothermia in the subject.

In an aspect, the present disclosure comprises methods of identifying in a subject a neural region suitable for targeted therapy, wherein the $A_1AR$ agonist crosses the blood brain barrier.

In an aspect, the present disclosure comprises methods of identifying in a subject a neural region suitable for targeted therapy, wherein the activation of the one or more neural regions is determined by cFos immunochemistry.

In an aspect, the present disclosure comprises methods of identifying in a subject a neural region suitable for targeted therapy, wherein the one or more $A_1AR$ agonists are administered in the winter and/or the summer.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc). Unless indicated otherwise, parts are parts by weight, temperature is in ° C. or is at ambient temperature, and pressure is at or near atmospheric.

Example 1: Adenosine and Hypothermia Induction

The data show a role for adenosine in regulating the onset of torpor and controlled reduction in thermogenesis and body temperature (Tb) (FIG. 1). Adenosine is a neuroprotective by-product of cellular metabolism that accumulates and is released from the brain during traumatic events (Dunwiddie and Masino, 2001). Under nonpathologic conditions, adenosine functions as a bioenergetic network regulator (Boison et al., 2011), and as a neuromodulator with key roles in sleep, thermoregulation and hibernation (Drew and Jinka, 2012) via a family of G protein-coupled receptors (GPCR). Torpor onset in the arctic ground squirrel (AGS) is regulated within the CNS by $A_1AR$ signaling and depends on a seasonal change in sensitivity to agonists (Jinka et al., 2011). Specifically, an $A_1AR$ agonist ($6^N$-cyclohexyladenosine or CHA) injected i.p. or delivered into the lateral ventricle (icv) induces torpor in winter, but not in summer. Moreover, CHA-induced torpor is similar to spontaneous torpor with regard to the magnitude and temporal profile of metabolic suppression and Tb decline. A seasonally regulated decrease in Tb during rest in euthermic (non-hibernating) AGS predicts onset of torpor and an increased hypothermic response to CHA. Thus, Tb in animals at rest is a biomarker of enhanced sensitivity to $A_1AR$ signaling (FIG. 2). This relationship between Tb and sensitivity to CHA is observed in rats as well as in AGS as disclosed herein.

Thus, adenosine contributes to homeostatic sleep through (1) global inhibition of cortical arousal (Beninton et al., 1995), (2) focal inhibition of hypothalamic cell groups that promote arousal, and (3) focal disinhibition of cell groups that promote sleep (Dworak et al., 2010). For example, stimulation of $A_1AR$ in the preoptic area of the hypothalamus (POAH) disinhibits sleep-active neurons within the ventrolateral preoptic (VLPO) and the median preoptic (MnPO) nuclei, and thereby promotes non REM and REM sleep (Szymusiak and McGinty, 2008). Adenosine also inhibits perifornical-lateral hypothalamus (PF-LH) and tuberomamillary nucleus (TMN) neurons directly to promote sleep (Alam et al., 2009; Rai et al, 2010).

The POAH plays a central role in thermoregulation as well as sleep regulation, and is therefore a particularly promising site for $A_1AR$-mediated control of torpor. The ventrolateral region of the medial POAH is activated during topor in the 13-lined ground squirrel, as evidenced by a pronounced increase in c-fos mRNA levels (Bratincsak et al., 2007). In addition, a number of studies have shown that thermoregulatory neurons in the POAH are sensitive to adenosine, and in particular to $A_1AR$ agonists. In rats, adenosine maintains Tb in part via $A_1AR$ activation in the POAH (Barros et al., 2006). Injection of the adenosine agonist CPA into the rat POAH lowers brain temperature when administered at doses slightly higher than doses found to induce sleep, and these effects are both mediated via activation of $A_1AR$ (Ticho and Radulovacki, 1991). Intracerebral injections of CHA in hamsters produced more marked decreases in Tb when injections were made in the anterior hypothalamus compared with other areas of the hypothalamus or forebrain (Shintani et al., 2005). Finally, rats fed a restricted diet have both reduced Tb and an increased sensitivity to the Tb-lowering effect of CHA injection, and that these effects are accompanied by up-regulation of $A_1AR$ surface expression in the hypothalamus, but not in the cortex (Jinka et al., 2010); this finding is consistent with the hypothalamus (and perhaps the POAH) as a site through which adenosine acts to regulate body temperature. The area postrema, the area subpostrema, and the dorsomedial nucleus of the solitary track are other brain regions through which adenosine can act to regulate body temperature and torpor (Tupone et al., 2013).

Example 2: $A_1AR$ Agonists Induce a Torpor-Like State in Diet Restricted Rats

In the AGS, Tb waxes and wanes according to a circannual rhythm that corresponds to the hibernation season. Troughs in Tb are seen at times when AGS display spontaneous torpor. Troughs in Tb also predict greater sensitivity to CHA (FIG. 2). The link between Tb and $A_1AR$ sensitivity seen in the AGS was also seen in rats. Rats fed every other day (dietary restriction; DR) show a decrease in Tb and an increased Tb-lowering effect of CHA (Jinka et al., 2010). These data indicate that similar mechanisms underlie increased sensitivity to CHA in AGS during the winter season and in rats fed a restricted diet.

Figure 2A:
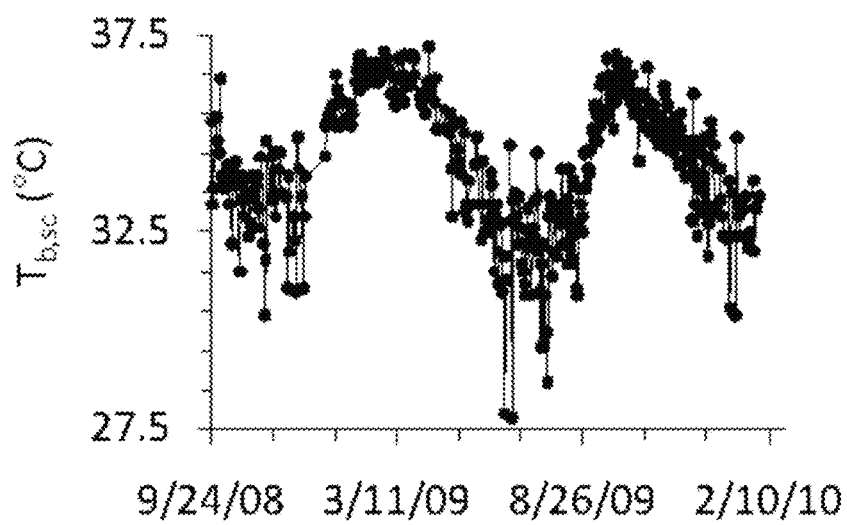
FIG. 2A-FIG. 2B show that AGS housed at ambient temperature (Ta) of 18° C., 12:12 L:D demonstrate a circannual rhythm in euthermic (nonhibernating) body temperature.
Figure 2B:
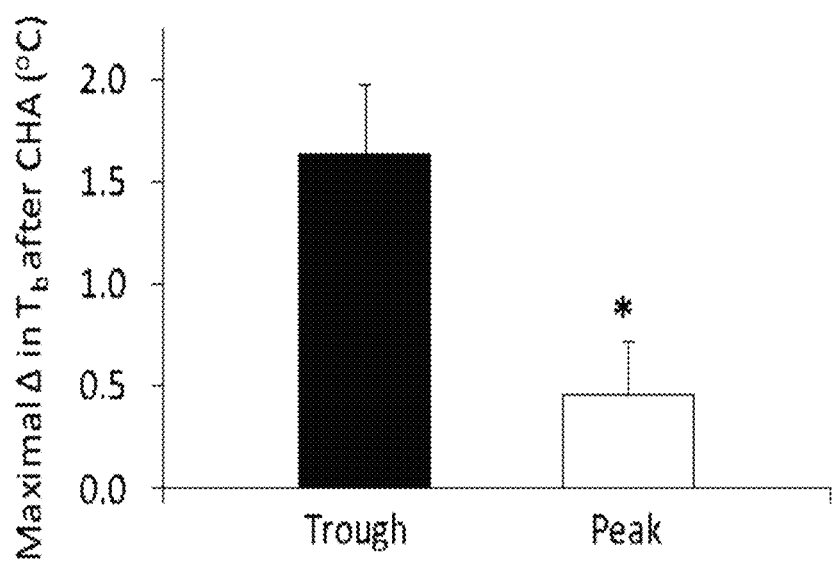

FIG. 2A shows a representative rhythm in subcutaneous body temperature (Tb,sc) in 1 of 24 AGS monitored over a two-year period. Spontaneous torpor is indicated by abrupt decreases in Tb,sc below about 30° C. FIG. 2B shows a maximal response to a low (non-torpor inducing) dose of CHA (0.1 mg/kg, i.p.) was greater when tested during a trough than when tested during a peak in euthermic Tb,sc (*p<0.05, t-test, n=6).

Figures 3A, 3B:
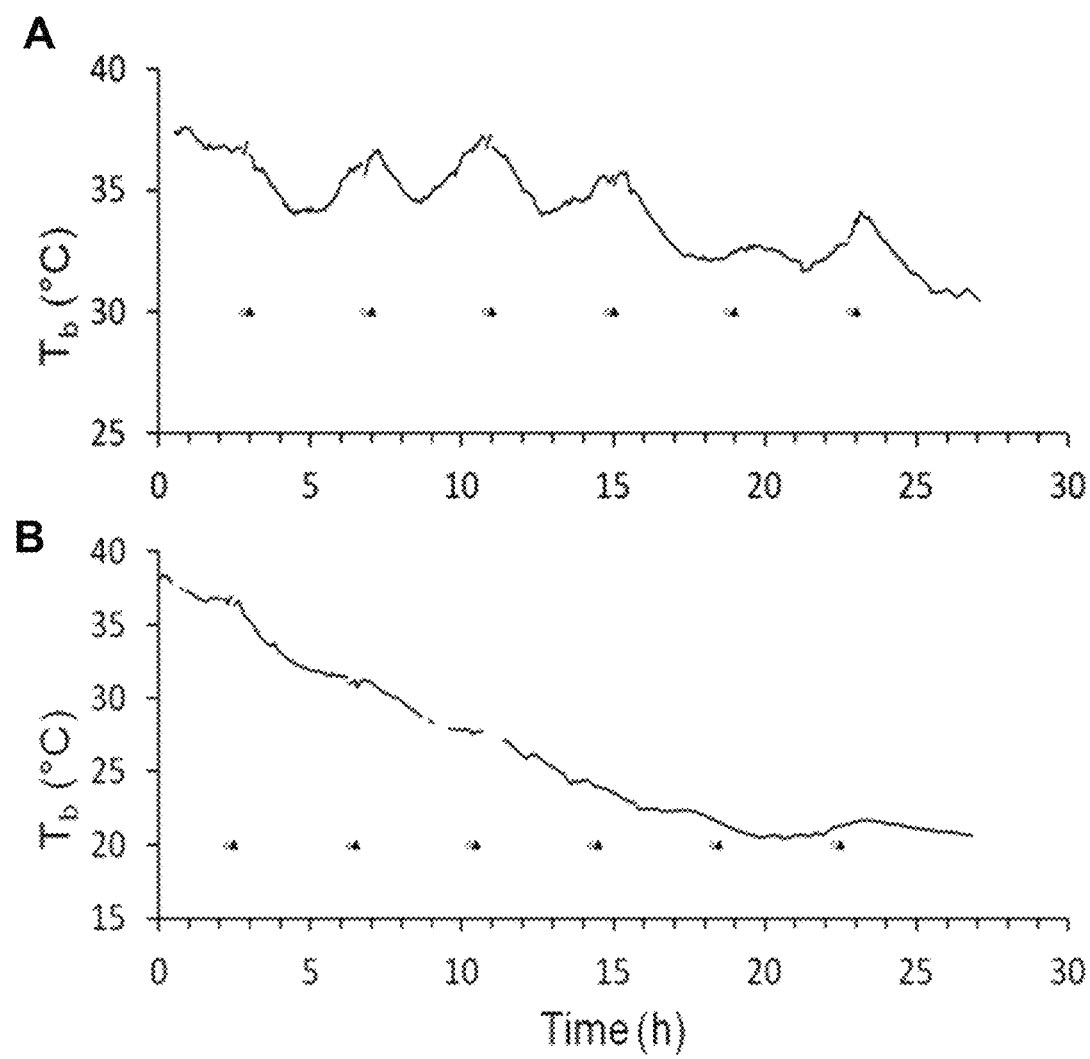
FIG. 3A-FIG. 3B show induction of therapeutic hypothermia in rats was achieved using intermittent injection of CHA and 8-SPT in ad libitum (AL) fed rats and dietary restricted (DR) rats.

Study of natural hibernation revealed two important principles relevant to therapeutic hypothermia. First, shivering is alleviated through stimulation of central $A_1AR$. Second, the Tb minimum and rate of cooling following stimulation of $A_1AR$ in the CNS can be controlled through manipulation of ambient temperature without external or internal cooling. These principles were used to develop methods for inducing hypothermia in dietary restricted (DR) rats (FIG. 3B). In FIG. 3, the magnitude and rate of cooling was controlled by adjusting ambient temperature (i.e., 16° C.) and regulating sensitivity to CHA through DR (every other day feeding, see FIG. 3B). Peripheral side effects were minimized by co-administration of 8-SPT (2.5 mg/kg i.p.) 15 min prior to CHA (0.5 mg/kg, i.p.). Drugs were administered at 4 hr intervals (indicated by tick marks), core Tb was measured using i.p. transmitters, n=1 per treatment. Subcutaneous temperatures in additional animals, n=2 per treatment yielded comparable results.

Data provided herein shows that repeated co-administration of CHA (an $A_1AR$ agonist that readily penetrates the blood brain barrier) and 8-p-sulfophenyltheophylline (8-SPT, a peripherally acting $A_1AR$ antagonist) produces an immediate decrease in Tb in conscious rats. Cooling is sustained and enhanced by repeated drug administration. The magnitude of cooling at a given dose of CHA is enhanced following DR where the response to CHA and 8-SPT resembles torpor in rate of cooling and in the way that Tb approaches ambient temperature. The ability to induce a torpor-like state in rats through the manipulation of adenosine signaling mechanisms indicates that (1) physiological mechanisms used by the AGS to reduce Tb during the onset of torpor are also present in non-hibernating species, and (2) these mechanisms can improve methods for inducing therapeutic hypothermia in humans.

Example 3: Induction of Therapeutic Hypothermia

Mild therapeutic hypothermia, in which core body temperature (Tb) is reduced to 32-34° C. for 24 hr or longer, is becoming the standard of care for cardiac arrest patients. However, technical challenges may limit the use of therapeutic hypothermia. Shivering is one of the most problematic issues in targeted temperature management (TTM) and is controlled with pharmacological adjuncts, such as paralytics, narcotics, sedatives or a combination of these such as meperidine and buspirone.

Here, $6^N$-cyclohexyladenosine (CHA), an $A_1AR$ agonist, induced hibernation as a pharmacological adjunct to facilitate effective techniques for TTM. Tb in hibernating ground squirrels can fall to as low as −3° C., which was through a process regulated by adenosine A1 receptor ($A_1AR$) signaling within the CNS, a mechanism common to other types of torpor. Evidence in rats indicates that activation of CNS $A_1AR$ with CHA suppresses shivering and nonshivering thermogenesis $A_1AR$ agonists protect against ischemic injury but have not been used clinically due to side effects, principally hypothermia, bradycardia and hypotension. Given the central site of action for $A_1AR$ mediated onset of hibernation and torpor as well as torpor-like hypothermia in rats, the present study shows that bradycardia can be managed by co-administration of an adenosine receptor antagonist that does not penetrate the blood brain barrier without interfering with the cooling effects of the drug. Finally, a rat model of cardiac arrest was used to show that this approach to TTM improves survival and decreases brain injury following cardiac arrest.

Methods

Sustained Hypothermia in Conscious Rats

Male Sprague-Dawley rats (2 to 3 months old, 375-400 g; obtained directly or derived from breeders obtained from Simonson Laboratories, Gilroy, Calif.) were housed in pairs at 20° C. on a 12L:12D photoperiod, fed ad libitum and allowed at least 2 weeks to acclimate before use.

Drug Delivery Via Sequential I.P. Injections

Animals were instrumented with IP IBUTTON® data loggers (Maxim Integrated, San Jose, Calif.) programmed to record body temperature (Tb) every 10 min and allowed 14 days post-operative recovery prior to drug testing. $6^N$-cyclohexyladenosine (CHA) was dissolved in 0.01 M phosphate buffer (PB); 8-(p-Sulfophenyl)theophylline (8-SPT) was dissolved in 0.9% saline and filter sterilized on the day of administration. PB for CHA and saline for 8-SPT were administered as vehicle controls where indicated. The day before the experiment, animals in both treatment and control groups were moved to an ambient temperature (Ta) of 16° C. and remained at this Ta until return to a Ta of 20° C., 4 hr after the last injection. Animals in the treatment group received a total of 6 injections of CHA (1.0 mg/kg, i.p.) every 4 hr, and a total of 6 injections of 8-SPT (25 mg/kg, ip), administered 15 min prior to each CHA injection. The control group received the same number of injections, with 8-SPT replaced by saline and CHA replaced by PB. Treatment and control conditions were tested in all animals with at least 1 week between experiments using a balanced cross-over design such that one-half of the animals received CHA and 8-SPT during the first experiment and the other received CHA and 8-SPT during the second experiment. Except for moving rats to a Ta of 20° C. 4 hr after the last injection no other means were used to facilitate rewarming. Neurological deficits, heart rate and hemoglobin oxygen saturation ($sO_2$) were measured 2 hr and immediately before injection, at 24 hr, after rewarming and daily for the next 3 days using a pulse oximeter applied to the hind paw (Vet/Ox TM 4402L; Sensor Devices, Waukesha, Wis.).

Drug Delivery Through iPRECIO® Pumps

To determine if the effects of CHA on heart rate were due to direct effects of CHA on the heart or to the effects of tissue temperature, programmable minipumps were employed to deliver CHA continuously for 24 hr at an ambient temperature of 25° C. and 16° C. During constant delivery of agonist the effects of 8-SPT on heart rate and $sO_2$ was also tested at 10 min intervals appropriate for the short half-life of the drug. For these experiments a separate group of rats was instrumented with programmable iPRECIO® pumps (DSI, St. Paul, Minn.). CHA was dissolved in 25% (w/v) hydroxypropyl-β-cyclodextrin (CD) in sterile water and 8-SPT was dissolved in 0.9% saline. Pumps delivered the same mass of CHA as in the first experiment (6 mg/kg over a 24 hr period), however, in this case CHA was delivered at a constant rate of 30 μL/hr. Heart rate (HR) and hemoglobin saturation ($sO_2$) was monitored using a pulse oximeter every 10 min for 1 hr following a single injection of 8-SPT (25 mg/kg, i.p.) or vehicle as indicated. As before, animals in both treatment and control groups were moved to an ambient temperature (Ta) of 16° C. or 25° C. the day before the experiment and remained at this Ta until return to a Ta of 20° C., 4 hr after the end of drug delivery. Drug and vehicle treatments were administered to all animals using a balanced cross-over design. At least 1 week separated CHA and vehicle (CD) treatment and 1 hr separated 8-SPT and vehicle (saline) injections.

Severity of Brain Injury Following 6 or 8 Min of Asphyxial Cardiac Arrest

Rats aged 69-75 days were subjected to 6 or 8 min of asphyxial cardiac arrest to establish the duration of asphyxia needed to produce significant loss of neurons in CA1 region of the hippocampus, an area most vulnerable to global cerebral ischemia/reperfusion.

Rats resuscitated within 120 sec were housed overnight in a neonatal incubator set to 29° C. Brains were collected 8 days after restoration of spontaneous circulation (ROSC) and processed for histopathology.

Therapeutic Benefit of Sustained Hypothermia in Conscious Rats Subjected to Asphyxial Cardiac Arrest Rats aged 68-75 days were subjected to 8 min of asphyxial cardiac arrest and animals that were resuscitated within 120 sec and met additional inclusion criteria 60 min after ROSC (Table 1) were randomly allocated to a therapeutic hypothermia (TH) or a normothermic control (NC) group using a computer-generated randomization schedule without knowledge of outcome. Treatment commenced 70 min after restoration of spontaneous circulation (ROSC).

TABLE 1

| Time From ROSC | Criteria for Inclusion for Random Assignment to Treatment |
|---|---|
| 2 min | ROSC within 120 sec |
| 30 min | Blood gases stable and within normal ranges; BE > 0 |
| 30-40 min | MABP ≥ 80 mm Hg |
| 60-70 min | Tb ≥ 33° C. |
| 70 min | Comatose (unresponsive to toe pinch) |

Animals assigned to the TH group were moved to 16° C. and CHA and 8-SPT delivered as described above for Drug delivery via sequential IP injections. Animals assigned to the NC group were moved to a neonatal incubator set to 29° C. and vehicles (PB and saline) delivered as described above for the control group. At the end of 24 hr the rats were moved to and housed an ambient temperature of 20° C. for 7 days until they were euthanized for tissue collection. Body temperature was monitored prior to each injection throughout treatment and daily thereafter using sc IPTT-300 transponders (BioMedic Data Systems, Inc. Seaford, Del.).

Asphyxial Cardiac Arrest (ACA)

ACA was induced as described by Dave et al., 2006. Animals were anesthetized with 5% isofluorane and a 30:70 mixture of $O_2$ and $N_2O$ followed by endotracheal intubation and mechanical ventilation. The femoral vein and artery were cannulated for continuous blood pressure monitoring and blood gas analysis. ECG leads were attached to the limbs. Physiological variables, including but not limited to $PaCO_2$, $PaO_2$, and pH were maintained within normal limits by adjusting respiratory rate and volume. MABP and ECG were monitored continuously. Temporalis muscle and rectal temperatures were maintained at 36.5-37.5° C. by heating lamps and Omega (Stamford, Conn.) T-CSC32 temperature controllers. To induce cardiac arrest, vecuronium (1 mg/kg) was injected I.V. and apnea was induced by disconnecting the ventilator from the endotracheal tube. Resuscitation was initiated by reconnecting the ventilator, administering epinephrine (0.01 mg/kg, I.V.) and sodium bicarbonate (1 mg/kg, I.V.) mechanically ventilating with 100% $O_2$ at a rate of 80 bpm and manual chest compressions until MABP reached 50 mm Hg and was maintained by a spontaneously beating heart for more than 10 sec. After 10 min of ROSC, ventilation was decreased to 60 bpm and $O_2$ lowered to 30%. Naïve animals were subjected to similar surgical procedures except that the ventilator was not disconnected from the endotracheal tube.

Post-Operative Care after Cardiac Arrest and During Hypothermia

Post-operative (post-op) rats subjected to 6 min and 8 min CA and not assigned to hypothermia experiments were placed in a neonatal incubator overnight with only water provided (0.9% saline, I.P. based off 1 mg/100 g body weight was injected at the end of surgery to prevent dehydration). After 8-16 hr, animals were fed, weighed, cleaned, and had neurological deficit scores (NDS) analyzed daily for 7 days beginning 2 hr post ROSC. Rats were fed a 50:50 mix of rodent chow and sugar mixed with water to create a soup, which was placed into small petri dishes to allow animals to self-feed. Animals that were unable to feed themselves were assisted via spoon-feeding. Spoon-feeding involved using a gavage needle and a 3 cc syringe to slowly and carefully inject the liquid soup material into the rat's mouth allowing their "swallow-reflex" to determine how much food was given. Rats in the hypothermia group recovered without need for post-op care.

Heart Rate and $sO_2$ Monitored Via Pulse Oximetry

A pulse oximeter (Vet/Ox SDI 4402L, Model 72042A3 Sensor Devices Inc., Lancaster, Pa.) was used to monitor heart rate (HR) and $sO_2$. Pulse oximetry was acquired via a sensor on the paw.

Neurological Deficit Scores

Behavioral Neurological Deficit Scores (NDS) were taken daily for 7 days after asphyxial cardiac arrest to assess injury. The total NDS consists of five components: consciousness and respiration, cranial nerve function, motor function, sensory function, and coordination (leg/tail movement, cleaning, depth perception, and righting reflex) as previously described in Katz et al., 1995). The NDS range is a scale between 0 (normal function) to 100 (brain dead).

Histology

Seven days post ROSC rats were perfused with FAM (a mixture of 40% formaldehyde, glacial acetic acid, and methanol, 1:1:8 by volume) for 19 min with an initial 1 min perfusion with physiological saline, both delivered through the ascending aorta. The perfusate is delivered at a constant rate of 80 mL/min into the left ventricle of the heart while clamping the descending aorta. Immediately after perfusion rats were decapitated and their heads stored in FAM for 24 hr at 4° C. On the next day, heads were washed in reverse osmosis water for 10-15 min, brains were removed from the skulls and stored in fresh FAM at 4° C. for another 24 hr. The following day brains were immersed in 70% ethanol solution until trimmed and sectioned into coronal brain blocks for paraffin embedding. For analysis, coronal sections of 6 μm were stained with hematoxylin and eosin. Sections containing hippocampus at the level of 3.8 mm posterior to bregma were examined. Healthy neuronal counts were made within the CA1 region of the hippocampus by an investigator blinded to the experimental conditions. CA1 counts were expressed as the number of normal neurons per millimeter of microscopic field at 40× magnification. Normal neurons were defined as having a well-defined cellular membrane and distinct cellular nucleus. MetaMorph 7.0 software was used to record cell counts.

Statistics

Data are reported as mean±SEM unless otherwise indicated. Data was analyzed by two-way analysis of variance (ANOVA) with repeated measures over time and Tukey post hoc comparisons (SAS, version.9.1.3) or t-test (Excel 2010) where indicated.

Results

CHA Induced a Decrease in Tb and Heart Rate

CHA (1.0 mg/kg, i.p.) decreased Tb to 33° C. within 1 hr (FIG. 4A). Data show that repeated injection of CHA at 4 hr intervals (which approximates the half-life of the drug) induces a steady minimum in Tb after the fourth injection (FIG. 4A). 8-SPT was administered 15 min prior to CHA. In FIG. 4A, ♦ indicates time of 8-SPT injection and ▲ indicates time of CHA injection. Vehicle injections [saline+ phosphate buffer (PB)] had no effect; Ta=16° C. All animals rewarmed within 3.5 hr after moving to a Ta of 20° C. without evidence of significant adverse events. FIG. 4B shows that neurological deficit scores (NDS) increased during hypothermia. At 24 hr, there was evidence of a slight, but statistically significant bradycardia in CHA-treated rats. (FIG. 4C). Heart rate remained significantly elevated 5.5 hr after the last CHA injection consistent with enhanced thermogenesis following cessation of CHA administration (FIG. 4C) (data shown are means±SEM, ★p<0.05 vs. veh [saline+ phosphate buffer (PB)], (Tukey test, n=6 per group)).

CHA-Induced Decrease in Tb Depended on Ta

Figure 5A:
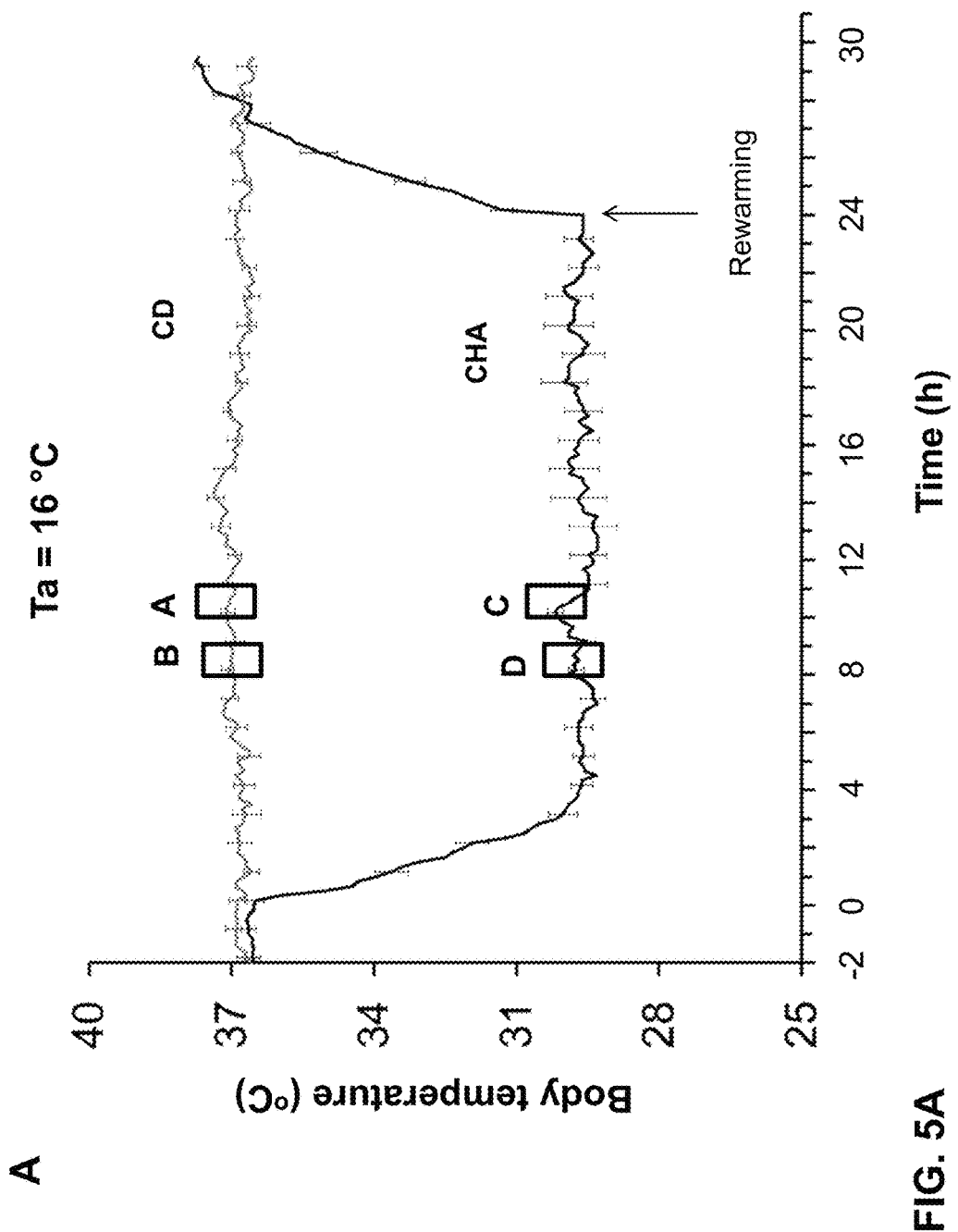
FIG. 5A-FIG. 5B show that continuous CHA delivery at 16° C. Ta produced stable hypothermia.
Figure 5B:
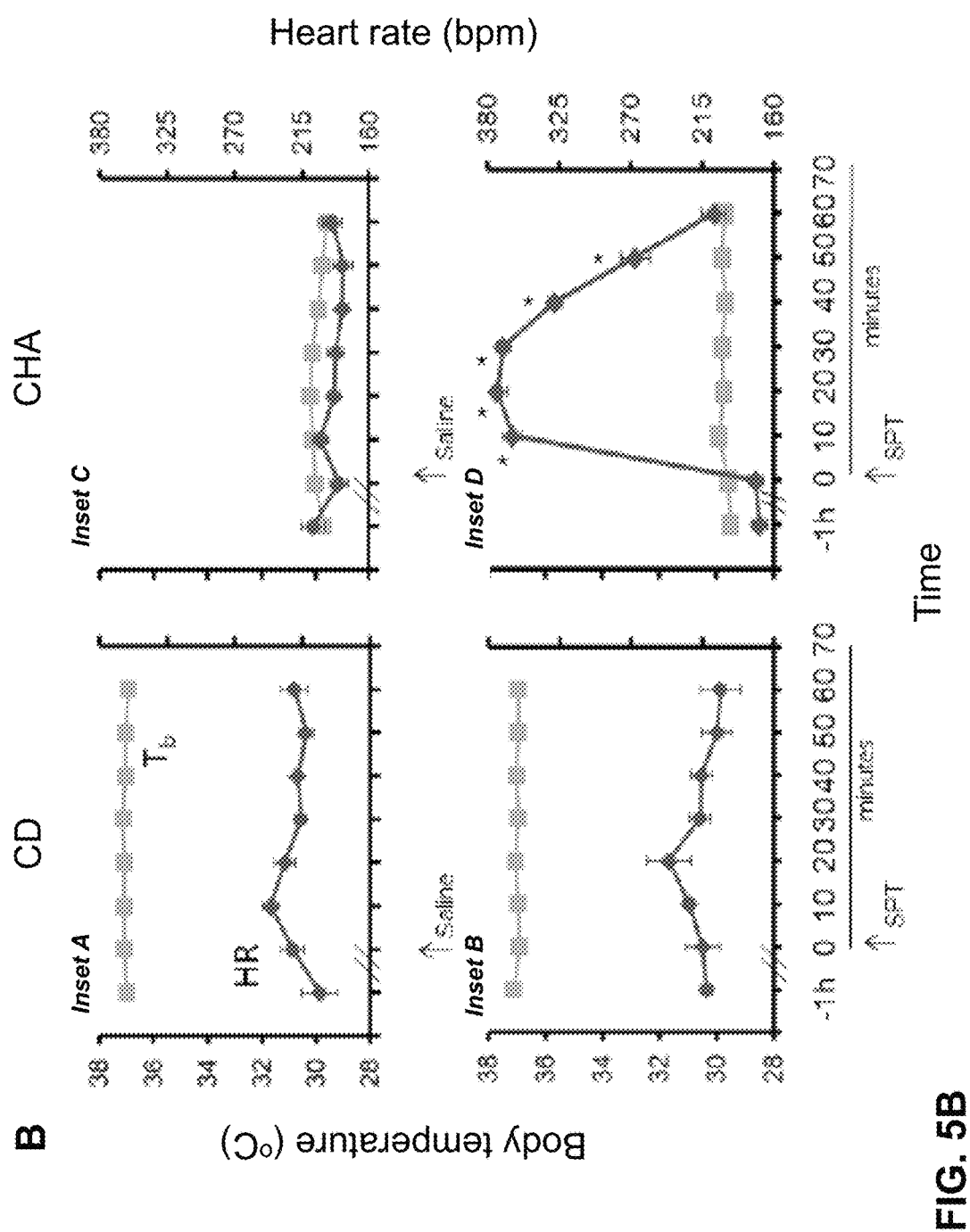
Figure 6A:
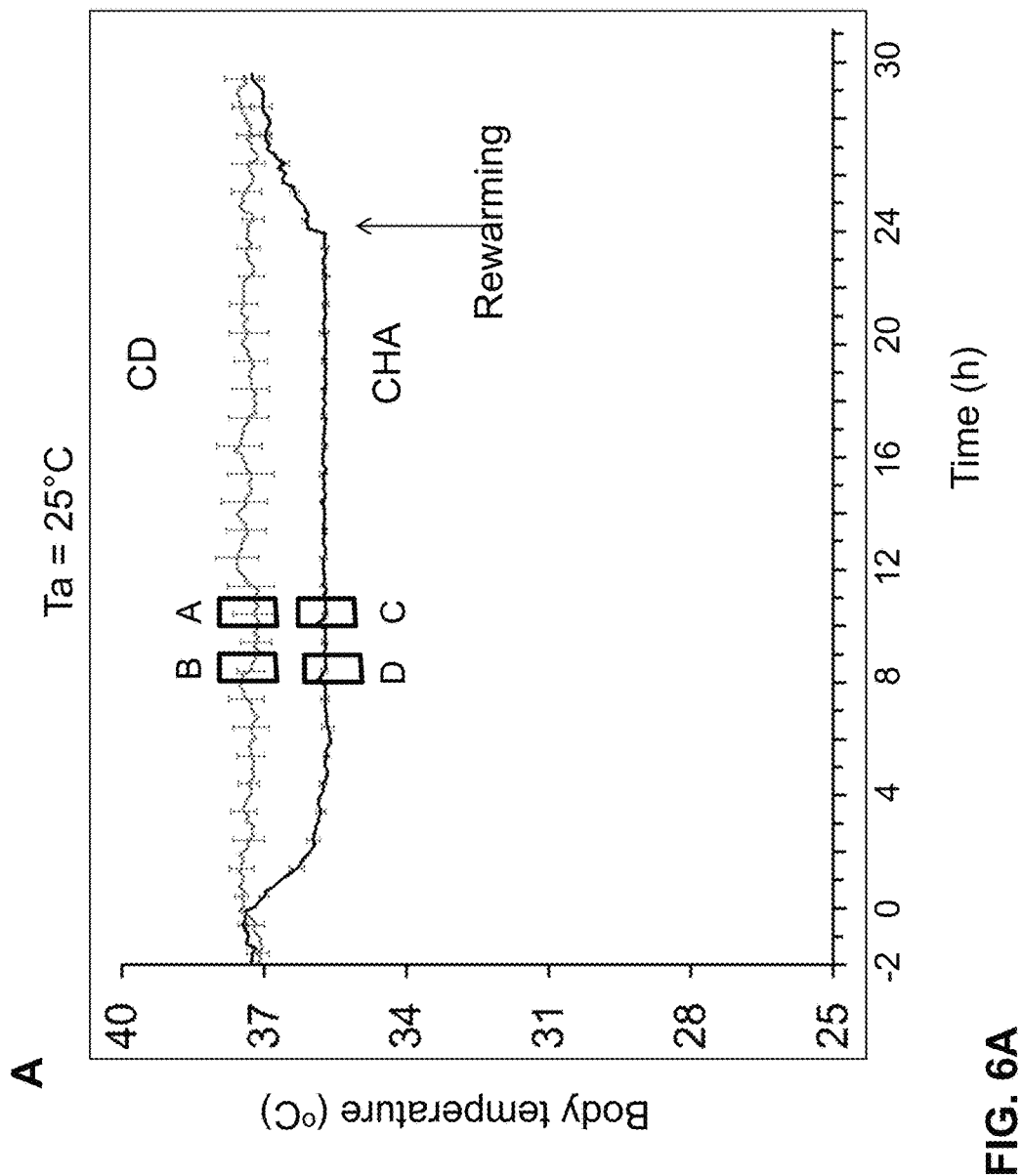
FIG. 6A-FIG. 6B show that continuous CHA delivery at 25° C. Ta produced stable hypothermia.

If CHA-induced cooling is due to inhibition of thermogenesis, then it was predicted that the magnitude of cooling should depend on the thermal gradient; i.e., the difference between Tb and Ta. To address this question, programmable mini-pumps were employed to deliver CHA continuously for 24 hr to rats housed at Ta of 16° C. or 25° C. Continuous CHA delivery (30 μL/hr) via a SQ minipump at a dose equivalent to 1 mg/kg every 4 hr at 16° C. Ta produced stable hypothermia (FIG. 5A; Insets A-D identified by boxes). FIG. 5B shows that 8-SPT (25 mg/kg, I.P.) delivered 8 hr after onset of CHA delivery (see Inset B and Inset D) increased heart rate without affecting body temperature. 8-SPT vehicle (saline) delivered 1 hr later had no effect (see Inset A and Inset C). ★ p<0.05 vs. analogous time point shown in FIG. 5 (Tukey test, n=5 per group). Results showed that continuous administration of CHA at Ta of 16° C. and 25° C. decreased Tb (p<0.0001) and heart rate (p<0.01; 3 way ANOVAs, main effects of group (CD vs CHA, FIG. 5, FIG. 6 with no effect on $sO_2$. Moreover, Tb was lowest at 16° C. At Ta of 16° C., the mean minimum Tb was 29.3±0.3° C. (FIG. 5A) and at Ta of 25° C., the mean minimum Tb was 35.6±0.12° C. (FIG. 6A).

$A_1AR$ Antagonist 8-SPT Reversed Bradycardia During Therapeutic Hypothermia without Affecting Tb.

The short half-life of 8-SPT (45 min in rabbit, Liu G S et al., 1991) indicated that heart rate measured 4 hr after 8-SPT administration did not reflect the effects of the drug. Thus it remained unclear if the decrease in heart rate after 24 hr of cooling, 4 hr after the last injection of 8-SPT and CHA (FIG. 4C) was due to direct effects of CHA or to tissue temperature. During the 24 hr period of continuous CHA administration, 8-SPT (or saline vehicle) was delivered and heart rate and $sO_2$ monitored for 60 min. At a Ta of 16° C., both 8-SPT and saline vehicle, delivered to control (CD treated) animals increased heart rate, presumably due to the stress of the injection (p=0.0434, 2-Way ANOVA, main effect of time, FIG. 5A-FIG. 5B). By contrast, in animals treated with CHA, 8-SPT, but not saline vehicle produced a 2 fold increase in heart rate (p<0.0001, 2 way ANOVA, time× treatment) with no influence on Tb. The effects of 8-SPT subsided within 60 min of drug administration.

Figure 6B:
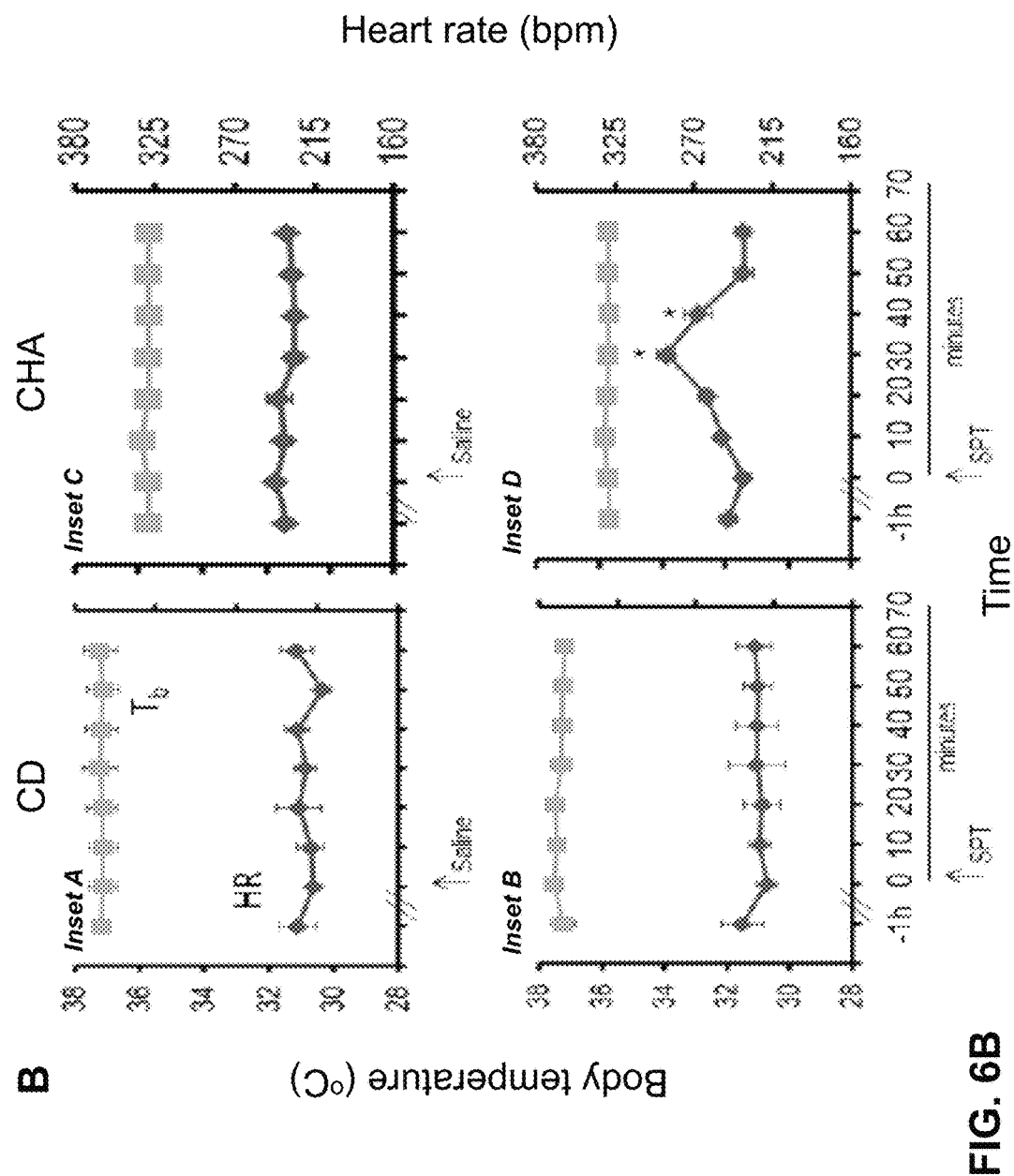

At a Ta of 25° C., 8-SPT and saline vehicle delivered to control (CD treated) animals had no effect on heart rate or Tb. By contrast, when 8-SPT was delivered to CHA treated animals, this $A_1AR$ antagonist produced a small, but significant increase in heart rate (p<0.0001, 2-way ANOVA, time×treatment) with no influence on Tb. Moreover, the magnitude of the effect of 8-SPT on heart rate was greater in animals housed at Ta of 16° C. than those housed at Ta of 25° C. (FIG. 5A-FIG. 5B for Ta of 16° C.; FIG. 6A-FIG. 6B for Ta of 25° C.). In FIG. 6, the continuous CHA delivery via a SQ minipump at a rate equivalent to 1 mg/kg every 4 hr at 25° C. Ta produced stable hypothermia (FIG. 6A; Insets A-D identified by boxes). FIG. 6B shows that 8-SPT (25 mg/kg, I.P.) delivered 8 hr after onset of CHA delivery (see Inset B and Inset D) increases heart rate without affecting body temperature. 8-SPT vehicle (saline) delivered 1 hr later had no effect (see Inset B and Inset D). ★p<0.05 (n=5).

The concept that CHA-induced TH in conscious rats improves survival and decreases brain damage following global cerebral ischemia was tested using a model of asphyxia cardiac arrest (ACA). Rats subjected to 6 or 8 min of asphyxia experienced similar degrees of global cerebral ischemia based on measures of MABP (FIG. 7A), heart rate, diastolic and systolic blood pressure except that ischemia lasted 2 min longer in rats exposed to the longer duration of asphyxia. Duration of 6 or 8 min produced similar decreases in the number of healthy CA1 neurons 8 days after restoration of spontaneous circulation (ROSC) (FIG. 7B and histology shown in FIG. 7C).

FIG. 8A shows that the mean arterial blood pressure (MABP) before, during, and after induction of 8 min asphyxial cardiac arrest was similar in rats subsequently assigned to therapeutic hypothermia (TH; ♦) (n=3) or normothermic control (NC; ■) (n=3) groups. The body temperature across time for the NC group is shown in FIG. 8B and the body temperature across time for the TH treated group is shown in FIG. 8C. Only 1 rat in the NC group survived to 7 days. At the onset of treatment, Tb was 33.5° C.±0.1 and 33.5° C.±0.1 in the NC (FIG. 8B) and TH (FIG. 8C) groups. Tb in all 3 NC rats increased to 36.5-36.8° C. within 15 min of placement at 29° C. and remained between 36.2° C. and 37.3° C. until death. Only 1 rat in the NC group survived to 8 days. The remaining 2 rats died between 13-18 hr after ROSC (FIG. 8). Tb in the 3 rats treated with TH decreased to 31.0 to 31.6° C. within 3 hr of CHA injection and remained between 31.8° C. and 29.2° C. for 24 hr before rewarming; individual Tb minima was 29.7±0.3° C. Rats rewarmed without intervention within 5 hr after transfer to a Ta of 20° C., 4 hr after the last injection of CHA. All 3 rats treated with TH survived to 8 days despite a decrease in MABP similar to the NC group (FIG. 8A).

Figure 9:
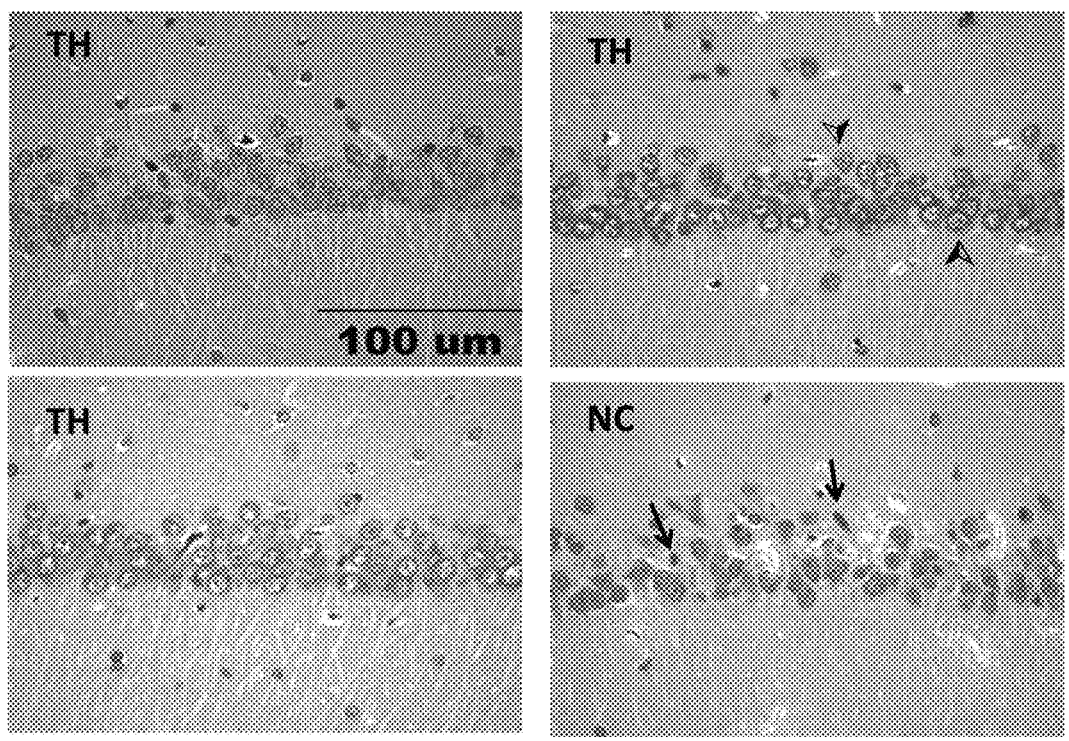
FIG. 9 shows representative histopathological images of pyknotic and healthy neurons in the CA1 hippocampal region of rates 8 days after 8 minutes of asphyxial cardiac arrest.

Histopathology showed ischemia-induced cell death in CA1 of hippocampus in the 1 normothermic control animal that survived to 8 days (FIG. 9). The CA1 in TH treated rats appeared similar to CA1 in naïve rats (FIG. 7C and FIG. 9) although comparison of healthy neuron counts revealed a significant difference. The number of healthy neurons per mm of CA1 (mean±SEM) was 135.5±4.6 for the TH group (n=3) and 180.8±12.3 for naïve rats (n=5; p=0.03, t-test) and 47.8 (n=1) for the normothermic control group. FIG. 9 provides representative images showing histopathology of pyknotic (ischemic; arrows) and healthy (normal; arrow heads) neurons in the CA1 hippocampal region of rats 8 days after 8 min asphyxial CA in TH and NC groups. Scale bar=100 µm.

Discussion

Results reported here show that the $A_1$ adenosine receptor ($A_1AR$) agonist $N^6$-cyclohexyladenosine (CHA), combined with a decrease in ambient temperature (Ta), is an effective adjunct for inducing therapeutic hypothermia (TH). Decreasing Ta to 16° C. and administering CHA intermittently or continuously produced a rapid and sustained decrease in core body temperature (Tb) with minimal effects on heart rate. Moreover, slight bradycardia was readily reversed with 8-p-sulfophenyltheophylline (8-SPT) which had no effect on Tb. Activation of $A_1ARs$ in the CNS can alone induce hibernation. The present results show that some of the torpor-inducing effects of CHA can translate to refined methods of facilitating hypothermia for therapeutic purposes.

CHA can facilitate onset of torpor by suppressing thermogenesis via activation of $A_1AR$ within the CNS. Core heat then dissipates at rates governed by ambient temperature and thermal conductance. The present results are consistent with this mechanism of action. The magnitude of CHA-induced cooling increased with a decrease in ambient temperature consistent with an inhibition of thermogenesis. Moreover, the cooling effect of CHA was mediated via the CNS since 8-SPT, a peripherally acting adenosine receptor antagonist did not reverse the effects of CHA on Tb. A recent study in rats shows that CHA acts within the NTS to inhibit shivering and nonshivering thermogenesis and to increase peripheral vasoconstriction and parasympathetic influence on the heart. These effects closely resemble the suite of thermoregulatory and autonomic nervous system changes that accompany onset of hibernation.

Pharmacological management of shivering and nonshivering thermogenesis is necessary for TTM to counter normal thermoregulatory mechanisms, especially shivering. Cold infusions alone do not keep patients cool. In comatose cardiac arrest patients, shivering is managed by a number of pharmacological adjuncts including a combination of meperidine and buspirone or other sedatives and narcotics as well as paralytics. But, shivering is significantly more difficult to control in conscious stroke patients. When shivering is not controlled, surface cooling can cause skin lesions. More importantly, shivering can prevent attainment of target temperature and contribute to adverse effects of TH. Difficulty controlling shivering complicates use of TH in comatose patients and limits benefit of TH in conscious patients.

Time to target temperature can influence outcome and thus control over time to target Tb is desired, even though optimal timing remains an area of active research. It is disclosed herein that combined pharmacological management of shivering and ambient temperature can be used to manage the rate of cooling and maintenance of hypothermia; animals cooled faster and to a lower Tb at the colder ambient temperature. In addition continuous administration of CHA produced a faster decline and a steadier minimum Tb when compared to intermittent injections. In the cardiac arrest model, cooling was initiated 70 min post ROSC and Tb reached a minimum 12 hr after ROSC. The data show, however, that the rate of cooling depends on the temperature differential; i.e., rate of cooling was faster at a Ta of 16° C. than at a Ta of 25° C. An advantage of CHA as a pharmacological adjunct is that in the hands of emergency medical technicians cooling can be initiated sooner than is currently feasible and achieved faster by applying ice or by taking advantage of cold ambient temperatures. Increased adenosine signaling immediately after traumatic brain injury contributes to respiratory depression and death. Caffeine, a nonselective adenosine receptor antagonist prevents acute mortality when administered immediately after traumatic brain injury. Moreover, a longer time between ROSC and target Tb was associated with a more favorable neurologic outcome in patients after cardiac arrest when compared to patients with a shorter time between ROSC and target Tb. Nonetheless, dependence of rate of cooling and Tb minimum on the temperature differential is consistent with other evidence that CHA produces a decrease in Tb by inhibiting thermogenesis and this mechanism of action, coupled with control of the heat sink, whether it be ice or ambient temperature, offers optimal control over time to target temperature.

In addition to effects on thermogenesis, $A_1AR$ agonists are neuroprotective in animal models of cardiac arrest. These direct effects within the CNS contributed to enhanced survival in the present study and contribute to therapeutic efficacy of these drugs if used as pharmacological adjuncts for TH. Therapeutic use of $A_1AR$ agonists is restricted by peripheral side effects, including negative chronotropic and dromotropic effects on the heart. The peripherally acting adenosine receptor antagonist, 8-SPT, reversed CHA-induced bradycardia. 8-SPT increased HR well above baseline noted in normothermic, vehicle treated animals. The results indicate that cooling produced an increase in norephineph-rine release from sympathetic nerve terminals innervating the heart and that this effect was greatest when Tb was lowest. The release of norepinephrine is modulated by presynaptic adenosine receptors. CHA likely inhibited norephinephrine release mitigating the influence of cold Tb on HR and this effect was reversed with 8-SPT. Despite the overshoot in correction in HR, the data show that bradycardia caused by systemic administration of CHA can be reversed with 8-SPT without influencing Tb or interfering with TH. A recent study shows that CHA suppresses thermogenesis through effects on the nucleus of the solitary tract and mimics increased parasympathetic tone characteristic of onset of torpor.

In sum, targeted activation of central $A_1AR$ as a pharmacological adjunct to TH is innovative because it mimics mechanisms utilized by mice and by hibernating species during onset of torpor. These studies establish the feasibility of maintaining prolonged periods of hypothermia in rats and show that Tb can be controlled by CHA and ambient temperature and that bradycardia can be reversed by a peripherally acting adenosine receptor antagonist.

REFERENCES

Alam M N, et al. (2009). Role of adenosine A(1) receptor in the perifornical-lateral hypothalamic area in sleep-wake regulation in rats. Brain Res. 1304:96-104.

Anderson R, et al. (1994). Characterization of the adenosine receptors mediating hypothermia in the conscious mouse. Br J Pharmacol. 113:1386-1390.

Arrich J, et al. (2009). Hypothermia for neuroprotection in adults after cardiopulmonary resuscitation. Cochrane Database Syst Rev. CD004128.

Barnes B M, (1989). Freeze avoidance in a mammal: Body temperatures below 0 degree c. in an arctic hibernator. Science. 244:1593-1595.

Barros R C, et al. (2006). Respiratory and body temperature modulation by adenosine A1 receptors in the anteroventral preoptic region during normoxia and hypoxia. Respir Physiol Neurobiol. 153:115-125.

Benington J H, et al. (1995). Stimulation of A1 adenosine receptors mimics the electroencephalographic effects of sleep deprivation. Brain Res. 692:79-85.

Bischofberger N, (1997). Adenosine a1 receptor agonists as clinically viable agents for treatment of ischemic brain disorders. Ann N Y Acad Sci. 825:23-29.

Blackstone E, et al. (2005). H2S induces a suspended animation-like state in mice. Science. 308, 518.

Boison D, et al. (2011). Homeostatic bioenergetic network regulation: a novel concept to avoid pharmacoresistance in epilepsy. Expert Opin Drug Discov. 6:1-12.

Bott-Flugel L, et al. (2011). Selective attenuation of norepinephrine release and stress-induced heart rate increase by partial adenosine a1 agonism. PLoS One. 6:e18048

Bratincsak A, et al. (2007). Spatial and temporal activation of brain regions in hibernation: c-fos expression during the hibernation bout in thirteen lined ground squirrel. J Comp Neurol. 505:443-458.

Buck C L, et al. (2000). Effects of ambient temperature on metabolic rate, respiratory quotient, and torpor in an arctic hibernator. Am J Physiol Regul Integr Comp Physiol. 279:R255-262.

Busto R, et al. (1987). Small differences in intraischemic brain temperature critically determine the extent of ischemic neuronal injury. J Cereb Blood Flow Metab. 7:729-738.

Cheung J W, et al. (2003). Cvt-510: A selective a1 adenosine receptor agonist. Cardiovasc Drug Rev. 21:277-292

Daniels I S, et al. (2010). A role of erythrocytes in adenosine monophosphate initiation of hypometabolism in mammals. J Biol Chem. 285:20716-20723.

Dave K R, et al. (2006). The arctic ground squirrel brain is resistant to injury from cardiac arrest during euthermia Stroke. 37(5):261-1265.

Dias da Silva V J. et al, (2012). Acute adenosine increases cardiac vagal and reduces sympathetic efferent nerve activities in rats. Exp Physiol.

Drew K L, et al. (2012). The bioenergetic network of adenosine in hibernation, sleep and thermoregulation. In Adenosine: a Key Link between Metabolism and CNS Activity, S. A. Masino, and D. Boison, eds. (New York, Springer).

Dunwiddie T V, et al. (2001). The role and regulation of adenosine in the central nervous system. Annu Rev Neurosci. 24:31-55.

Dworak M, et al. (2010). Sleep and brain energy levels: ATP changes during sleep. J Neurosci. 30:9007-9016.

Evoniuk G, et al. (1987). Antagonism of the cardiovascular effects of adenosine by caffeine or 8-(p-sulfophenyl) theophylline. J Pharmacol Exp Ther. February; 240(2): 428-32.

Faridar A, et al. (2011). Therapeutic hypothermia in stroke and traumatic brain injury. Front Neurol. 2; 80.

Geiser F, (1988). Reduction of metabolism during hibernation and daily torpor in mammals and birds: Temperature effect or physiological inhibition? J Comp Physiol B. 158:5-37.

Gerashchenko D, et al. (2011). Sleep-active cells in the cerebral cortex and their role in slow-wave activity. Sleep Biol Rhythms. 9:71-77.

Harris M B, et al. (1995). Parasympathetic influence on heart rate in euthermic and hibernating ground squirrels. J Exp Biol. 198:931-937.

Haugk M, et al. (2011). Relationship between time to target temperature and outcome in patients treated with therapeutic hypothermia after cardiac arrest. Crit Care. 15:R101.

Heller H C, et al. (1977) Thermoregulation during entrance into hibernation. Pflügers Arch. 369:55-59.

Hypothermia-after-Cardiac-Arrest-Study-Group (2002). Mild therapeutic hypothermia to improve the neurologic outcome after cardiac arrest. N Engl J Med. 346:549-556.

Iliff B W, et al. (2012). Central adenosine receptor signaling is necessary for daily torpor in mice. Am J Physiol Regul Integr Comp Physiol. 303:R477-484.

Jinka T R, et al. (2011). Season primes the brain in an arctic hibernator to facilitate entrance into torpor mediated by adenosine a(1) receptors. J Neurosci. 31:10752-10758.

Jinka T R, et al. (2010). Altered thermoregulation via sensitization of A1 adenosine receptors in dietary-restricted rats. Psychopharmacology (Berl). 209:217-224.

Jordan J D, et al. (2007). Hypothermia: comparing technology. J Neurol Sci. 261:35-38.

Katz L, et al. (1995). Outcome model of asphyxial cardiac arrest in rats. J Cereb Blood Flow Metab. 15:1032-1039.

Kliegel A, et al. (2007). Cold infusions alone are effective for induction of therapeutic hypothermia but do not keep patients cool after cardiac arrest. Resuscitation. 73:46-53.

Korboukh I, et al. (2012). Orally active adenosine a(1) receptor agonists with antinociceptive effects in mice. J Med Chem. 55:6467-6477.

Kumar S, et al. (2011). Central nervous system sites of the sleep promoting effects of eszopiclone in rats. Neuroscience. 181:67-78.

Liu G S, et al. (1991). Protection against infarction afforded by preconditioning is mediated by a1 adenosine receptors in rabbit heart. Circulation. 84:350-356.

Logan A, et al. (2011). Optimal management of shivering during therapeutic hypothermia after cardiac arrest. Crit Care Nurse. 31:e18-30.

Lusardi T A, et al. (2012). Caffeine prevents acute mortality after TBI in rats without increased morbidity. Exp Neurol. 234:161-168.

Lyman C P, et al. (1963). Autonomic control of circulation during the hibernating cycle in ground squirrels. J Physiol. 168:477-499.

Olson J M, et al. (2013). Circannual rhythm in body temperature, torpor, and sensitivity to a(1) adenosine receptor agonist in arctic ground squirrels. J Biol Rhythms. 28:201-207.

Paxinos G, et al. (1989). The Rat Brain in Stereotaxic Coordinates, 2nd Edn. (Sidney, Academic Press).

Porkka-Heiskanen T, et al. (2011). Adenosine, energy metabolism and sleep homeostasis. Sleep Med Rev. 15:123-135.

Rai S, et al. (2010). A1 receptor mediated adenosinergic regulation of perifornical-lateral hypothalamic area neurons in freely behaving rats. Neuroscience. 167:40-48.

Rittiner J E, et al. (2012). Amp is an adenosine a1 receptor agonist. J Biol Chem. 287:5301-5309.

Sessler D I, et al. (2009). Defeating normal thermoregulatory defenses: induction of therapeutic hypothermia. Stroke. 40:e614-621.

Seupaul R A, et al. (2011). Evidence-based emergency medicine. Does therapeutic hypothermia benefit survivors of cardiac arrest? Ann Emerg Med. 58:282-283.

Shao C, et al. (2010). Shotgun proteomics analysis of hibernating arctic ground squirrels. Mol Cell Proteomics. 9:313-326.

Shin R, et al. (2010). Administration of the GABAA receptor antagonist picrotoxin into rat supramammillary nucleus induces c-Fos in reward-related brain structures. Supramammillary picrotoxin and c-Fos expression. BMC Neurosci 11:101.

Shintani M, et al. (2005). Characterization of N(6)-cyclohexyladenosine-induced hypothermia in Syrian hamsters. J Pharmacol Sci. 97:451-454.

Swoap S J, et al. (2007). AMP does not induce torpor. Am J Physiol Regul Integr Comp Physiol. 293:R468-473.

Szymusiak R, et al. (2008). Hypothalamic regulation of sleep and arousal Ann N Y Acad Sci. 1129:275-286.

Tamura Y, et al. (2005) Phase-specific central regulatory systems of hibernation in Syrian hamsters. Brain Res. 1045:88-96.

Testori C, et al. (2011). Surface cooling for induction of mild hypothermia in conscious healthy volunteers—a feasibility trial. Crit Care. 15:R248.

Ticho S R, et al. (1991). Role of adenosine in sleep and temperature regulation in the preoptic area of rats. Pharmacol Biochem Behav. 40:33-40.

Toien O, et al. (2011). Hibernation in black bears: independence of metabolic suppression from body temperature. Science. 331:906-909.

Tupone D, et al. (2013) Central activation of the a1 adenosine receptor (a1ar) induces a hypothermic, torpor-like state in the rat. J Neurosci. 33:14512-14525.

Uray T, et al. (2008). Out-of-hospital surface cooling to induce mild hypothermia in human cardiac arrest: A feasibility trial. Resuscitation. 77:331-338.

Walker J M, et al. (1977). Sleep and hibernation in ground squirrels (*Citellus* spp): electrophysiological observations. Am J Physiol. 233:R213-221.

Walker J M, et al. (1980). Hibernation and circannual rhythms of sleep. Physiological Zoology. 53:8-11.

Xu K, et al. (2006). Adenosine treatment delays postischemic hippocampal CA1 loss after cardiac arrest and resuscitation in rats. Brain Res. 1071:208-217.

Zgavc T, et al. (2011). Experimental and clinical use of therapeutic hypothermia for ischemic stroke: Opportunities and limitations. Stroke Res Treat. 2011:689290.

Zhang J, et al. (2006). Constant darkness is a circadian metabolic signal in mammals. Nature. 439:340-343.

Zhao H W, et al. (2006). Distribution of NMDA receptor subunit NR1 in arctic ground squirrel central nervous system. J Chem Neuroanat. 32:196-207.

What is claimed is:

1. A method of treating ischemic brain injury caused by cardiac arrest in a subject comprising administering to the subject a therapeutically effective amount of an $A_1$ adenosine receptor ($A_1AR$) agonist and an $A_1AR$ antagonist, wherein the $A_1AR$ agonist is capadenoson, or a combination of capadenoson with $N^6$-cyclohexyladenosine (CHA), and the $A_1AR$ antagonist is 8-p-sulfophenyltheophylline (8-SPT), wherein the $A_1AR$ agonist crosses the blood brain barrier and wherein the $A_1AR$ antagonist does not cross the blood-brain barrier, and wherein treating ischemic brain injury involves alleviating shivering in the subject.

2. The method of claim 1, further comprising inducing therapeutic hypothermia in the subject.

3. The method of claim 2, further comprising maintaining hypothermia in the subject.

4. The method of claim 3, wherein maintaining hypothermia in the patient comprises repeating the administration of the $A_1AR$ agonist and the $A_1AR$ antagonist.

5. The method of claim 1, wherein the $A_1AR$ agonist and the $A_1AR$ antagonist are co-administered.

6. The method of claim 1, wherein the $A_1AR$ antagonist is titrated to minimize side effects of the agonist.

7. A method of controlling core body temperature in a subject comprising administering to the subject a therapeutically effective amount of an $A_1AR$ agonist and an $A_1AR$ antagonist, wherein the $A_1AR$ agonist is capadenoson or a combination of capadenoson with CHA, and the $A_1AR$ antagonist is 8-SPT, wherein the $A_1AR$ agonist crosses the blood brain barrier and wherein the $A_1AR$ antagonist does not cross the blood-brain barrier, wherein the A1AR agonist alleviates shivering.

8. The method of claim 7, wherein the subject had an ischemic brain injury.

* * * * *